(12) United States Patent
Tavazoie et al.

(10) Patent No.: US 9,040,497 B2
(45) Date of Patent: May 26, 2015

(54) TREATMENT AND DIAGNOSIS OF COLON CANCER

(71) Applicant: THE ROCKEFELLER UNIVERSITY, New York, NY (US)

(72) Inventors: Sohail F. Tavazoie, New York, NY (US); Jia M. Loo, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 14/480,098

(22) Filed: Sep. 8, 2014

(65) Prior Publication Data

US 2014/0378534 A1    Dec. 25, 2014

Related U.S. Application Data

(63) Continuation of application No. PCT/US2013/067860, filed on Oct. 31, 2013.

(60) Provisional application No. 61/720,912, filed on Oct. 31, 2012, provisional application No. 61/786,500, filed on Mar. 15, 2013.

(51) Int. Cl.
| | |
|---|---|
| *A61K 31/197* | (2006.01) |
| *A61K 31/513* | (2006.01) |
| *A61K 31/7072* | (2006.01) |
| *A61K 31/337* | (2006.01) |
| *A61K 31/4168* | (2006.01) |
| *A61K 31/4745* | (2006.01) |
| *A61K 31/555* | (2006.01) |
| *A61K 31/7068* | (2006.01) |
| *A61K 31/7088* | (2006.01) |
| *A61K 45/06* | (2006.01) |
| *A61K 31/70* | (2006.01) |

(52) U.S. Cl.
CPC ........... *A61K 31/197* (2013.01); *A61K 31/7072* (2013.01); *A61K 31/337* (2013.01); *A61K 31/4168* (2013.01); *A61K 31/4745* (2013.01); *A61K 31/513* (2013.01); *A61K 31/555* (2013.01); *A61K 31/7068* (2013.01); *A61K 31/7088* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,324,731 A | 6/1994 | Kaddurah-Daouk et al. | |
| 5,676,978 A | 10/1997 | Teicher et al. | |
| 6,288,124 B1 * | 9/2001 | Kaddurah-Daouk | 514/634 |

FOREIGN PATENT DOCUMENTS

WO    2011158667 A1    12/2011

OTHER PUBLICATIONS

Ohira et al. Biochimica et Biopysica Acta vol. 1097(2):117-122, 1991.*
Bergnes et al. Oncology Research vol. 8(3):121-130, 1996.*
Li et al., "miR495 and miR-551a inhibit the migration and invasion of human gastric cancer cells by directly interacting with PRL-3," Cancer Lett (Mar. 30, 2012); 323(1):41-7.

* cited by examiner

*Primary Examiner* — Sean McGarry
(74) *Attorney, Agent, or Firm* — Fox Rothschild LLP; Gerard P. Norton; Jianming Jimmy Hao

(57) ABSTRACT

The present invention discloses novel agents and methods for diagnosis and treatment of colon cancer. Also disclosed are related arrays, kits, and screening methods.

26 Claims, 7 Drawing Sheets

TREATMENT AND DIAGNOSIS OF COLON CANCER

CROSS REFERENCE TO RELATED APPLICATIONS

This application is Continuation of International Application No. PCT/US13/67860, filed on Oct. 31, 2013, which claims priority of U.S. Provisional Application No. 61/720,912 filed on Oct. 31, 2012 and U.S. Provisional Application No. 61/786,500 filed on Mar. 15, 2013. The contents of these applications are incorporated herein by reference in their entireties.

GOVERNMENT INTERESTS

The invention disclosed herein was made, at least in part, with Government support under Grant No. 1 DP2 OD006506-01 from the National Institutes of Health. Accordingly, the U.S. Government has certain rights in this invention.

FIELD OF THE INVENTION

This invention relates to diagnosis and treatment of colon cancer.

BACKGROUND OF THE INVENTION

Colon cancer, commonly known as colorectal cancer or bowel cancer, is a cancer from uncontrolled cell growth in the colon or rectum, or in the appendix. See e.g., Cancer Genome Atlas Network, "Comprehensive molecular characterization of human colon and rectal cancer," Nature 487: 330-337 (19 Jul. 2012). It is the second most frequently diagnosed malignancy in the United States and the second most common cause of cancer death. For example, the five-year survival rate for patients with colorectal cancer detected in an early localized stage is 92% while the survival rate drops to 64% if the cancer is allowed to spread to adjacent organs or lymph nodes, and to 7% in patients with distant metastases.

The prognosis of colon cancer is directly related to the degree of penetration of the tumor through the bowel wall and the presence or absence of nodal involvement. Consequently, early detection and treatment are important. Currently, diagnosis is aided by the use of screening assays for fecal occult blood, sigmoidoscopy, colonoscopy and double contrast barium enemas. Treatment regimens, as determined by the type and stage of the cancer, include surgery, radiation therapy and/or chemotherapy. Yet, recurrence following surgery (the most common form of therapy) is a major problem and often the ultimate cause of death. Despite research into therapies for the disease, colon cancer remains difficult to diagnose and treat. Thus, there is a need for new agents and methods for detecting and treating colon cancer.

SUMMARY OF INVENTION

This invention addresses the above-mentioned need by providing agents and methods for diagnosis and treatment of colon cancer.

In one aspect, the invention features a method for treating colon cancer (e.g., metastatic colon cancer) in a subject in need thereof. The method includes increasing in the subject the expression level of a microRNA selected from the group consisting of miR-483-5p and miR-551a. The increasing step can be carried out by administering to the subject a nucleic acid encoding miR-483-5p or miR-551a. The nucleic acid can be an oligonucleotide, e.g., a synthetic nucleic acid. The nucleic acid can be in a vector, such as one selected from the group consisting of a plasmid, virus, cosmid, artificial chromosome, and other vehicles derived from bacterial and/or viral sources. Examples of the virus include Adeno Associated Virus (AAV) or POX virus. The Adeno Associated Virus or POX virus can be modified to increase activity, stability, or specificity. In some examples, the nucleic acid contains the sequence of any one of SEQ ID NOs: 1-10 or the complement thereof. The method can further include administering to the subject an additional therapeutic agent as disclosed herein.

In a second aspect, the invention provides an isolated RNA interference (RNAi) agent capable of inhibiting expression of Creatine Kinase Brain-type (CKB) or creatine transporter channel SLC6a8 (SLC6a8). The agent contains a first nucleotide sequence that is homologous or complement to a region of a gene encoding the CKB or SLC6a8 protein. In some examples, the first nucleotide sequence includes the sequence of any one of SEQ ID NOs: 11-18.

The invention also provides an isolated nucleic acid comprising a sequence encoding the RNAi agent mentioned above and a vector having the nucleic acid. The vector can be one selected from the group consisting of a plasmid, virus, cosmid, artificial chromosome, and other vehicles derived from bacterial and/or viral sources. Preferably, the vector is a viral vector, e.g., an AAV viral vector. Also provided is a host cell having above-mentioned the RNAi agent, nucleic acid, or vector. Further provided is a pharmaceutical composition having (a) a pharmaceutically acceptable carrier and (b) the RNAi agent, the nucleic acid, or the vector. The RNAi agent, the nucleic acid, or the vector can be complexed with other agents, e.g., liposomal compounds or polyethyleneamine, for efficient delivery. In one embodiment, the pharmaceutical composition further contains an additional therapeutic agent.

In a third aspect, the invention features a method for treating cancer, such as colon cancer (e.g., metastatic colon cancer) or pancreatic cancer in a subject in need thereof. The method includes decreasing in the subject the expression level or activity of CKB or SLC6a8). The decreasing step can be carried out by administering to the subject a nucleic acid, a small molecule compound, or both. In one example, the decreasing step is carried out by administering to the subject cyclocreatine or beta-guanidinopropionic acid. In others, the decreasing step is carried out by administering to the subject one agent selected from the group consisting of the above-described RNAi agent, nucleic acid, and vector. In some embodiments, the method further includes administering to the subject an additional therapeutic agent, such as beta-guanidinopropionic acid.

The invention also features a method for treating cancer such as colon cancer and pancreatic cancer in a subject in need thereof. The method includes decreasing in the subject the level of creatine through inhibition of the creatine transporter channel SLC6a8. The method includes administering to the subject beta-guanidinopropionic acid, and, optionally, an additional therapeutic agent. Examples of the additional therapeutic agent include one or more selected from the group consisting of the above mentioned cyclocreatine, RNAi agent, nucleic acid, and vector. Additional examples of additional therapeutic agents include 5-fluorouracil, Oxaliplatin, Irinotecan, Capecitabine, Gemcitabine, Cetuximab, Taxol, Avastin, folinic acid (leucovorin), Regorafenib, Zaltrap, topoisomerase I inhibitors, NKTR-102, Tivantinib, PX-866, Sorafenib, Linifanib, kinase inhibitors, Telatinib, XL281 (BMS-908662), Robatumumab and IGF1-R inhibitors.

In a fourth aspect, the invention provides a method for determining whether a subject has, or is at risk of having, metastatic colon cancer. The method includes (i) obtaining from the subject a sample; (ii) measuring in the sample the expression level of a microRNA selected from the group consisting of miR-483-5p and miR-551a; and (ii) comparing the expression level with a predetermined reference value. The subject is determined to have, or to be at risk of having, metastatic colon cancer if the expression level is below the predetermined reference value. The predetermined reference value can be obtained from a control subject that does not have metastatic colon cancer. The sample can be a body fluid sample or a biopsy tumor sample. The method can also be used for determining whether a subject has, or is at risk of having, recurrence of metastatic colon cancer, or for determining whether a subject has, or is at risk of having, colon cancer or metastatic colon cancer that is resistant to chemotherapeutics or targeted therapies. More specifically, the subject is determined to have, or be at risk of having recurrence of metastatic colon cancer, or colon cancer or metastatic colon cancer that is resistant to chemotherapeutics or targeted therapies, if the expression level is below the predetermined reference value.

In a fifth aspect, the invention provides an array having (i) a support having a plurality of unique locations and (ii) any combination of at least one nucleic acid having a sequence that is complementary to miR-483-5p, miR-551a, or an expression product (e.g., mRNA or related cDNA) of the gene encoding CKB or SLC6a8. For example, nucleic acid can be complementary to or, under a stringent hybridization condition, hybridize with one of SEQ ID NOs: 1-18. Each nucleic acid is immobilized to a unique location of the support.

The invention also provides a kit for diagnosing a metastatic potential of colon cancer in a subject, the potential for metastatic colon cancer to recur, the potential for metastatic colon cancer to progress rapidly, or the potential for metastatic colon cancer to display resistance to chemotherapy. The kit contains a reagent that specifically binds to miR-483-5p, miR-551a, or an expression product (e.g., mRNA, cDNA, and polypeptide) of the gene encoding CKB or SLC6a8. The agent can be a probe having a sequence complementary to the sequence of miR-483-5p and miR-551a. For example, each probe can have a sequence that is complementary to or, under a stringent hybridization condition, hybridize with one of SEQ ID NOs: 1-18. The kit can further include reagents for performing a hybridization assay or a PCR assay or the array mentioned above.

In a sixth aspect, the invention provides a method of identifying a compound useful for treating colon cancer or for inhibiting cancer cell survival, hypoxic survival, metastatic survival, or metastatic colonization. The method includes (i) obtaining a test cell expressing a microRNA selected from the group consisting of miR-483-5p and miR-551a; (ii) exposing the test cell to a test compound; (iii) measuring the expression level of the microRNA in the test cell; (iv) comparing the expression level with a control level; and (v) selecting the test compound as a candidate useful for treating colon cancer or for inhibiting cancer cell survival, hypoxic survival, metastatic survival, or metastatic colonization, if the comparison indicates that the expression level is higher than the control level.

The invention also provides a method of identifying a compound useful for treating colon cancer or for inhibiting cancer cell survival, hypoxic survival, metastatic survival, or metastatic colonization. The method includes (i) obtaining a test cell capable of expressing a polypeptide or mRNA of a gene selected from the group consisting of CKB or SLC6a8; (ii) exposing the test cell to a test compound; (iii) measuring the expression level of the gene in the test cell; (iv) comparing the expression level with a control level; and (v) selecting the test compound as a candidate useful for treating colon cancer or for inhibiting cancer cell survival, hypoxic survival, metastatic survival, or metastatic colonization, if the comparison indicates that the expression level is lower than the control level.

In the above-descried methods, the control level can be obtained from a control cell that is the same as the test cell except that the control cell has not been exposed to the test compound. The test cell can be a cell of a colon cancer cell line, e.g., LS-174T human colon cancer line. In some embodiments, the expression level of the gene can be measured using a reporter construct where a report gene (e.g., one encoding luciferase, GFP, or LacZ) is operably linked to a promoter of the gene encoding the above-mentioned miR-483-5p, miR-551a, CKB, or SLC6a8.

This invention further provides a method for treating breast cancer, gastric cancer, pancreatic cancer, esophageal cancer, liver cancer, gallbladder cancer, prostate cancer, sarcoma cancer, melanoma, or lung cancer in a subject in need thereof. The method includes, among others, administering to the subject beta-guanidinopropionic acid.

The details of one or more embodiments of the invention are set forth in the description below. Other features, objects, and advantages of the invention will be apparent from the description and from the claims.

DETAILED DESCRIPTION OF THE INVENTION

Figure 1:
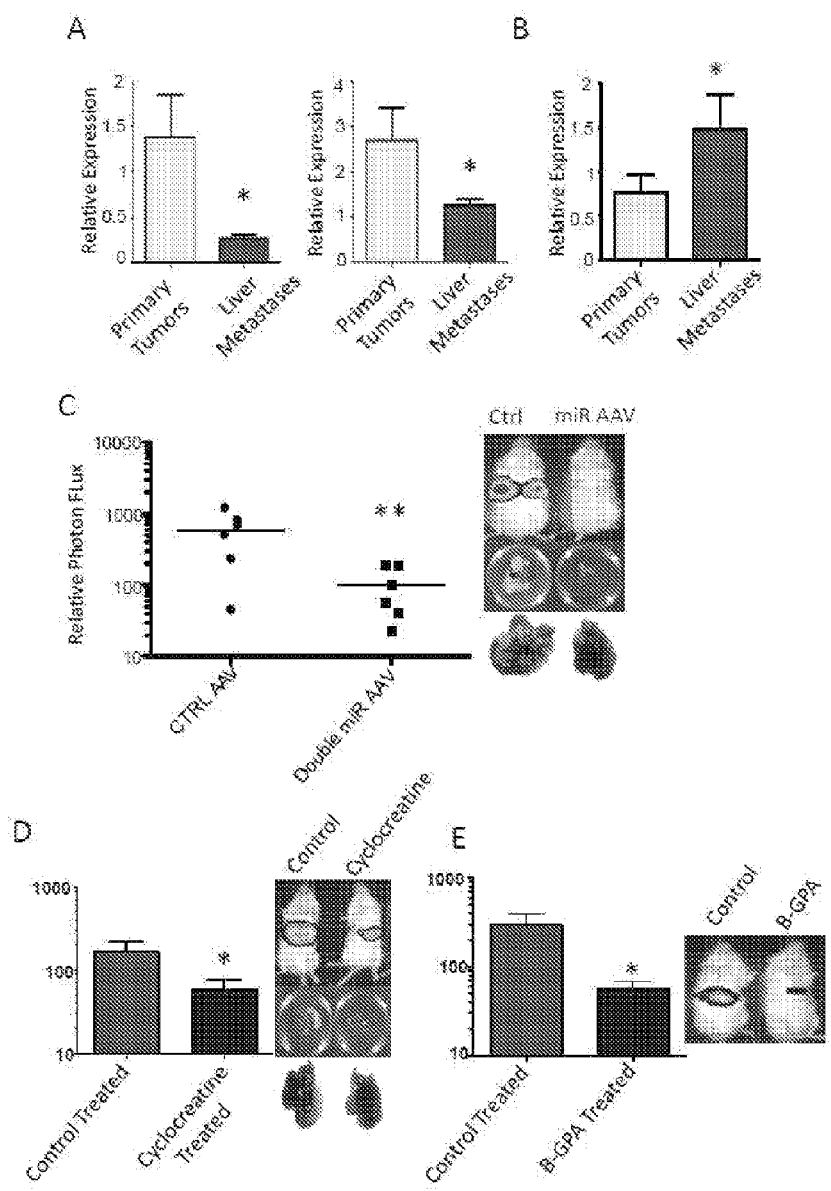
FIGS. 1A-E are a set of diagrams and photographs showing that miR-483-5p, miR-551a and CKB are clinically relevant and can be therapeutically inhibited. a, miR-483-5p and miR-551a levels in 37 primary tumor samples and 30 liver metastases samples were quantified by quantitative real-time PCR. b, CKB expression levels in 37 primary tumor samples and 30 liver metastases samples were measured by quantitative real-time PCR. c, Liver metastasis in mice injected with LvM3b cells and treated with a single dose of AAV doubly expressing miR-483-5p and miR-551a one day after injection cells. d, Bioluminescent measurements of liver metastasis in mice injected with $5\times10^5$ LvM3b cells and treated with cyclocreatine daily for two weeks. Mice were euthanized and livers excised for ex vivo imaging at the end of the treatment. e, Bioluminescent measurements of liver metastasis in mice injected with $5\times10^5$ LvM3b cells and treated with the creatine transporter inhibitor beta-guanidinopropionic acid (B-GPA) daily for two weeks. Error bars, s.e.m; all P values are based on one-sided Student's t-tests. *P<0.05; P<0.001; *P<0.0001.

The invention is based, at least in part, on unexpected discoveries that a cooperative miRNA-protein network is deregulated in liver colonization by metastatic colon cancer and that miRNAs, e.g., miR-483-5p and miR-551a, suppress colon cancer metastatic survival by cooperatively targeting brain creatine kinase dependent energetics. Accordingly, this invention provides new agents and methods for diagnosis and treatment of colon cancer, in particular metastatic colon cancer.

The colonization of an organ by disseminated cancer cells represents the final, most clinically significant, and least understood stage of cancer progression. The liver is a highly common organ for such metastatic colonization by many cancer types. To understand the molecular basis of liver colonization, an in vivo selection model of liver colonization by colon cancer was established. It is a powerful system as it couples competitive intra-organ in-vivo selection with small-RNA profiling to functionally assess the in vivo roles of 611 microRNAs in parallel during liver colonization. As disclosed herein, endogenous miR-483-5p and miR-551a were identified as robust suppressors of liver metastatic colonization by multiple colon cancer populations of diverse mutational backgrounds. These miRNAs are epigenetically silenced in metastatic cells and in human liver metastases and suppress metastasis by targeting creatine kinase, brain-type (CKB).

As disclose herein, CKB promotes metastasis by enhancing the survival of disseminated cancer cells in the liver—where they encounter hepatic hypoxia. Colon cancer survival is dependent on CKB production of phospho-creatine, which acts as an energetic store for generating ATP needed to endure hepatic hypoxia. Consistent with this, inhibiting cancer cell creatine uptake through creatine transporter knockdown also reduces metastasis. Therapeutic administration of miR-483-5p and miR-551 through adeno-associated viral delivery dramatically suppresses colon cancer metastasis. Additionally, therapeutic targeting of CKB with a small-molecule inhibitor significantly suppresses colon cancer metastasis. These results highlight the significance of metabolic energetics in sustaining metastatic survival during cancer progression. The findings disclosed herein have important implications for the treatment of gastrointestinal malignancies, which preferentially colonize the liver and claim the lives of over 500,000 people per year. Moreover, the in vivo screening/selection approach disclosed herein has the potential to comprehensively and rapidly identify coding and non-coding genes regulating colonization of any organ by any cancer type.

As disclosed herein, via the above-mentioned approach, a set of miRNAs were identified to be deregulated in human metastatic lines of colon cancer. As disclosed herein, miR-483-5p and miR-551a act as robust endogenous suppressors of colon cancer metastasis through convergent targeting of the metabolic gene Creatine Kinase Brain-type (CKB). These miRNAs display significant prognostic capacity in identifying patients that develop colon cancer metastatic relapse, while therapeutic delivery of these miRNAs significantly inhibits colon cancer metastasis.

The members of the miRNA-protein network disclosed herein can be used as s targets for treating metastatic colon cancer. In addition, the members can be used a biomarkers for determining whether a subject has, or is at risk of having, a metastatic colon cancer or for determining a prognosis or surveillance of patient having the disorder. Accordingly, the present invention encompasses methods of treating metastatic colon cancer by targeting one or more of the members, methods of determining the efficacy of therapeutic regimens for inhibiting the cancer, and methods of identifying anti-cancer agents. Also provided are methods of diagnosing whether a subject has, or is at risk for having, metastatic colon cancer, and methods of screening subjects who are thought to be at risk for developing the disorder. The invention also encompasses various kits suitable for carrying out the above mentioned methods.

Treatment Methods

As disclosed herein, miR-483-5p and miR-551a were identified as endogenous metastasis suppressors of cancer cell survival, hypoxic survival, metastatic survival, or metastatic colonization in colon cancer and other types of cancers while CKB and creatine transporter channel SLC6a8, function as metastasis promoters of the same process. These miRNAs or proteins not only strongly predict human metastatic outcomes but also provide targets for treating cancers such as colon cancer and other types of cancers.

Accordingly, this invention provides methods of using related agents, including, microRNAs, RNAi agents targeting CKB, RNAi agents targeting SLC6a8, vectors (e.g., AAV) encoding such an RNAi agent, cyclocreatine, and Guanidinoproprionic acid in treating cancers such as colon cancer and other types of cancers via increasing in the subject the expression level or activity level of one or more of the metastasis suppressors. This increasing can be achieved by, among others, forced expression of one or more of the metastasis suppressors. In addition, the treatment can be achieved by decreasing the expression level or activity level of one or more of the metastasis promoters. Examples of other types of cancers include solid tumors, particularly carcinomas. Exemplary solid tumors include, but are not limited to, carcinomas of the lung, breast, bone, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, mesotheleoma melanomas, myeloma, lymphoma gliomas, glioblastomas, neuroblastomas, Kaposi's sarcoma, and sarcomas. In particular, the methods of this invention can be used in treating gastric cancer, esophageal cancer, pancreatic cancer, liver cancer, biliary tract cancer, and breast cancer.

Forced Expression of Metastasis Suppressors

Both miR-483-5p and miR-551a and nucleic acid encoding them can be used as metastasis suppressors to practice the invention by overexpression of them in cells of interest or a subject in need thereof.

"Overexpression" refers to the expression of a RNA or polypeptide encoded by a nucleic acid introduced into a host cell, wherein the RNA or polypeptide or protein is either not normally present in the host cell, or wherein the RNA or polypeptide is present in said host cell at a higher level than that normally expressed from the endogenous gene encoding the RNA or polypeptide.

All of naturally occurring versions, genetic engineered versions, and chemically synthesized versions of the above-mentioned suppressors can be used to practice the invention disclosed therein. For expressing the above-mentioned suppressors, the invention provides a nucleic acid that encodes any of the suppressors mentioned above. Preferably, the nucleotide sequences are isolated and/or purified. A nucleic acid refers to a DNA molecule (e.g., but not limited to, a cDNA or genomic DNA), an RNA molecule (e.g., but not limited to, an mRNA), or a DNA or RNA analog. A DNA or RNA analog can be synthesized from nucleotide analogs. The nucleic acid molecule can be single-stranded or double-stranded. An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

The terms "RNA," "RNA molecule," and "ribonucleic acid molecule" are used interchangeably herein, and refer to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA also can be chemically synthesized. DNA and RNA can be single-stranded (i.e., ssRNA and ssDNA, respectively) or multi-stranded (e.g., double-stranded, i.e., dsRNA and dsDNA, respectively).

The present invention also provides recombinant constructs having one or more of the nucleotide sequences described herein. Example of the constructs include a vector, such as a plasmid or viral vector, into which a nucleic acid sequence of the invention has been inserted, in a forward or reverse orientation. In a preferred embodiment, the construct further includes regulatory sequences, including a promoter, operably linked to the sequence. Large numbers of suitable vectors and promoters are known to those of skill in the art, and are commercially available. Appropriate cloning and expression vectors for use with prokaryotic and eukaryotic hosts are also described in Sambrook et al. (2001, Molecular Cloning: A Laboratory Manual, Cold Spring Harbor Press).

Examples of expression vectors include chromosomal, nonchromosomal and synthetic DNA sequences, e.g., derivatives of or Simian virus 40 (SV40), bacterial plasmids, phage DNA, baculovirus, yeast plasmids, vectors derived from combinations of plasmids and phage DNA, viral DNA such as vaccinia, adenovirus, fowl pox virus, and pseudorabies. However, any other vector may be used as long as it is replicable and viable in the host. The appropriate nucleic acid sequence may be inserted into the vector by a variety of procedures. In general, a nucleic acid sequence encoding one of the suppressors described above can be inserted into an appropriate restriction endonuclease site(s) by procedures known in the art. Such procedures and related sub-cloning procedures are within the scope of those skilled in the art.

The nucleic acid sequence in the aforementioned expression vector is preferably operatively linked to an appropriate transcription control sequence (promoter) to direct RNA synthesis. Examples of such promoters include: the retroviral long terminal (LTR) or SV40 promoter, the $E.\ coli$ lac or trp promoter, the phage lambda PL promoter, and other promoters known to control expression of genes in prokaryotic or eukaryotic cells or viruses. The expression vector can also contain a ribosome binding site for translation initiation, and a transcription terminator. The vector may include appropriate sequences for amplifying expression. In addition, the expression vector preferably contains one or more selectable marker genes to provide a phenotypic trait for selection of transformed host cells such as dihydrofolate reductase or neomycin resistance for eukaryotic cell cultures, or such as tetracycline or ampicillin resistance in $E.\ coli$.

The vector containing the appropriate nucleic acid sequences as described above, as well as an appropriate promoter or control sequence, can be employed to transform an appropriate host to permit the host to express the suppressor described above. Such vectors can be used in gene therapy. Examples of suitable expression hosts include bacterial cells (e.g., $E.\ coli$, $Streptomyces$, $Salmonella\ typhimurium$), fungal cells (yeast), insect cells (e.g., $Drosophila$ and $Spodoptera\ frugiperda$ (Sf9)), animal cells (e.g., CHO, COS, and HEK 293), adenoviruses, and plant cells. The selection of an appropriate host is within the scope of those skilled in the art. In some embodiments, the present invention provides methods for producing the above mentioned suppressor by transfecting a host cell with an expression vector having a nucleotide sequence that encodes one of the suppressors.

Decreasing Expression or Activity Level of Metastasis Promoters

As mentioned above, one can use an inhibitory agent that decreases the expression or activity level of CKB or SLC6a8 in treating colon cancer. An inhibitory agent (i.e., inhibitor) can be a nucleic acid, a polypeptide, an antibody, or a small molecule compound. In one example, the inhibitor functions at a level of transcription, mRNA stability, translation, protein stability/degradation, protein modification, and protein binding.

A nucleic acid inhibitor can encode a small interference RNA (e.g., an RNAi agent) that targets one or more of the above-mentioned genes, e.g., CKB or SLC6a8, and inhibits its expression or activity. The term "RNAi agent" refers to an RNA, or analog thereof, having sufficient sequence complementarity to a target RNA to direct RNA interference. Examples also include a DNA that can be used to make the RNA. RNA interference (RNAi) refers to a sequence-specific or selective process by which a target molecule (e.g., a target gene, protein or RNA) is down-regulated. Generally, an interfering RNA ("iRNA") is a double stranded short-interfering RNA (siRNA), short hairpin RNA (shRNA), or single-stranded micro-RNA (miRNA) that results in catalytic degradation of specific mRNAs, and also can be used to lower or inhibit gene expression.

The term "short interfering RNA" or "siRNA" (also known as "small interfering RNAs") refers to an RNA agent, preferably a double-stranded agent, of about 10-50 nucleotides in length, preferably between about 15-25 nucleotides in length, more preferably about 17, 18, 19, 20, 21, 22, 23, 24, or 25 nucleotides in length, the strands optionally having overhanging ends comprising, for example 1, 2 or 3 overhanging nucleotides (or nucleotide analogs), which is capable of directing or mediating RNA interference. Naturally-occurring siRNAs are generated from longer dsRNA molecules (e.g., >25 nucleotides in length) by a cell's RNAi machinery (e.g., Dicer or a homolog thereof).

The term "miRNA" or "microRNA" refers to an RNA agent, preferably a single-stranded agent, of about 10-50 nucleotides in length, preferably between about 15-25 nucleotides in length, more preferably about 17, 18, 19, 20, 21, 22, 23, 24, or 25 nucleotides in length, which is capable of directing or mediating RNA interference. Naturally-occurring miRNAs are generated from stem-loop precursor RNAs (i.e., pre-miRNAs) by Dicer. The term "Dicer" as used herein, includes Dicer as well as any Dicer orthologue or homologue capable of processing dsRNA structures into siRNAs, miRNAs, siRNA-like or miRNA-like molecules. The term microRNA (or "miRNA") is used interchangeably with the term "small temporal RNA" (or "stRNA") based on the fact that naturally-occurring microRNAs (or "miRNAs") have been found to be expressed in a temporal fashion (e.g., during development).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region.

Within the scope of this invention is utilization of RNAi featuring degradation of RNA molecules (e.g., within a cell). Degradation is catalyzed by an enzymatic, RNA-induced silencing complex (RISC). A RNA agent having a sequence sufficiently complementary to a target RNA sequence (e.g., the above-mentioned CKB or SLC6a8 gene) to direct RNAi means that the RNA agent has a homology of at least 50%, (e.g., 50%, 60%, 70%, 80%, 90%, 95%, 98%, 99%, or 100% homology) to the target RNA sequence so that the two are sufficiently complementary to each other to hybridize and trigger the destruction of the target RNA by the RNAi machinery (e.g., the RISC complex) or process. A RNA agent having a "sequence sufficiently complementary to a target RNA sequence to direct RNAi" also means that the RNA agent has a sequence sufficient to trigger the translational inhibition of the target RNA by the RNAi machinery or process. A RNA agent also can have a sequence sufficiently complementary to a target RNA encoded by the target DNA sequence such that the target DNA sequence is chromatically silenced. In other words, the RNA agent has a sequence sufficient to induce transcriptional gene silencing, e.g., to down-modulate gene expression at or near the target DNA sequence, e.g., by inducing chromatin structural changes at or near the target DNA sequence.

The above-mentioned polynucleotides can be delivered using polymeric, biodegradable microparticle or microcapsule delivery devices known in the art. Another way to achieve uptake of the polynucleotides is using liposomes, prepared by standard methods. The polynucleotide can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano, et al., 1995, J. Mol. Med. 73:479). Alternatively, tissue specific targeting can be achieved by the use of tissue-specific transcriptional regulatory elements that are known in the art. Delivery of naked DNA (i.e., without a delivery vehicle) to an intramuscular, intradermal, or subcutaneous site is another means to achieve in vivo expression.

siRNA, miRNA, and asRNA (antisense RNA) molecules can be designed by methods well known in the art. siRNA, miRNA, and asRNA molecules with homology sufficient to provide sequence specificity required to uniquely degrade any RNA can be designed using programs known in the art, including, but not limited to, those maintained on websites for AMBION, Inc. and DHARMACON, Inc. Systematic testing of several designed species for optimization of the siRNA, miRNA, and asRNA sequence can be routinely performed by those skilled in the art. Considerations when designing short interfering nucleic acid molecules include, but are not limited to, biophysical, thermodynamic, and structural considerations, base preferences at specific positions in the sense strand, and homology. These considerations are well known in the art and provide guidelines for designing the above-mentioned RNA molecules.

An antisense polynucleotide (preferably DNA) of the present invention can be any antisense polynucleotide so long as it possesses a base sequence complementary or substantially complementary to that of the gene encoding a component of the aforementioned network. The base sequence can be at least about 70%, 80%, 90%, or 95% homology to the complement of the gene encoding the polypeptide. These antisense DNAs can be synthesized using a DNA synthesizer.

The antisense DNA of the present invention may contain changed or modified sugars, bases or linkages. The antisense DNA, as well as the RNAi agent mentioned above, may also be provided in a specialized form such as liposomes, microspheres, or may be applied to gene therapy, or may be provided in combination with attached moieties. Such attached moieties include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof (e.g., cholesteryl chloroformate, cholic acid, etc.). These moieties may be attached to the nucleic acid at the 3' or 5' ends thereof and may also be attached thereto through a base, sugar, or intramolecular nucleoside linkage. Other moieties may be capping groups specifically placed at the 3' or 5' ends of the nucleic acid to prevent degradation by nucleases such as exonuclease, RNase, etc. Such capping groups include, but are not limited to, hydroxyl protecting groups known in the art, including glycols such as polyethylene glycol, tetraethylene glycol and the like. The inhibitory action of the antisense DNA can be examined using a cell-line or animal based gene expression system of the present invention in vivo and in vitro.

Nucleic acids encoding one or more of the RNAi agents mentioned above or polypeptide suppressors (to be discussed below) can be cloned in a vector for delivering to cells in vitro or in vivo. For in vivo uses, the delivery can target a specific tissue or organ (e.g., liver or colon). Targeted delivery involves the use of vectors (e.g., organ-homing peptides) that are targeted to specific organs or tissues after systemic administration. For example, the vector can have a covalent conjugate of avidin and a monoclonal antibody to a liver specific protein.

In certain embodiments, the present invention provides methods for in vivo expression the above-mentioned metastasis suppressors. Such method would achieve its therapeutic effect by introduction of nucleic acid sequences encoding any of the factors into cells or tissues of a human or a non-human animal in need of inhibiting cancer cell survival, hypoxic survival, metastatic survival, or metastatic colonization. Delivery of the nucleic acid sequences can be achieved using a recombinant expression vector such as a chimeric virus or a colloidal dispersion system. Preferred for therapeutic delivery of the nucleic acid sequences is the use of targeted liposomes.

Various viral vectors which can be utilized for gene therapy disclosed herein include, adenovirus, adeno-associated virus (AAV), herpes virus, vaccinia, or, preferably, an RNA virus such as a retrovirus and a lentivirus. Preferably, the retroviral vector is a lentivirus or a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using a target-specific antibody or hormone that has a receptor in the target. Those of skill in the art will recognize that specific polynucleotide sequences can be inserted into the retroviral genome or attached to a viral envelope to allow target specific delivery of the retroviral vector.

Another targeted system for delivery of nucleic acids is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA, and intact virions can be encapsulated within the aqueous interior and delivered to cells in a biologically active form. Methods for efficient gene transfer using a liposome vehicle are known in the art. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidyl-ethanolamine, sphingolipids, cerebrosides, and gangliosides. Exemplary phospholipids include egg phosphatidylcholine, dipalmitoylphosphatidylcholine, and distearoyl-phosphatidylcholine. The targeting of liposomes is also possible based on, for example, organ-specificity, cell-specificity, and organelle-specificity and is known in the art.

When used in vivo, it is desirable to use a reversible delivery-expression system. To that end, the Cre-loxP or FLP/FRT system and other similar systems can be used for reversible delivery-expression of one or more of the above-described nucleic acids. See WO2005/112620, WO2005/039643, U.S. Applications 20050130919, 20030022375, 20020022018, 20030027335, and 20040216178. In particular, the reversible delivery-expression system described in US Application NO 20100284990 can be used to provide a selective or emergency shut-off.

In another example, the above-mentioned inhibitory agent or suppressor can be a polypeptide or a protein complex, such as an antibody or its antigen-binding portion, which inhibits or otherwise interferes with the activity of CKB or SLC6a8.

The term "antibody" refers to an immunoglobulin molecule or immunologically active portion thereof, i.e., an antigen-binding portion. Examples include, but are not limited to, a protein having at least one or two, heavy (H) chain variable regions ($V_H$), and at least one or two light (L) chain variable regions ($V_L$). The $V_H$ and $V_L$ regions can be further subdivided into regions of hypervariability, termed "complementarity determining regions" ("CDR"), interspersed with regions that are more conserved, termed "framework regions" (FR). As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, and IgG4), delta, epsilon and mu constant region genes, as well as the myriad immunoglobulin variable region genes.

The term "antigen-binding portion" of an antibody (or "antibody portion") refers to one or more fragments of an antibody that retain the ability to specifically bind to an antigen (e.g., CKB or SLC6a8). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

Antibodies that specifically bind to one of the above-mentioned target proteins (e.g., CKB or SLC6a8) can be made using methods known in the art. This antibody can be a polyclonal or a monoclonal antibody. In one embodiment, the antibody can be recombinantly produced, e.g., produced by phage display or by combinatorial methods. In another embodiment, the antibody is a fully human antibody (e.g., an antibody made in a mouse which has been genetically engineered to produce an antibody from a human immunoglobulin sequence), a humanized antibody, or a non-human antibody, for example, but not limited to, a rodent (mouse or rat), goat, primate (for example, but not limited to, monkey), rabbit, or camel antibody. Examples of methods to generate humanized version of antibodies include, but are not limited to, CDR grafting (Queen et al., U.S. Pat. No. 5,585,089; Riechmann et al., Nature 332:323 (1988)), chain shuffling (U.S. Pat. No. 5,565,332); and veneering or resurfacing (EP 592,106; EP 519,596); Padlan, Molecular Immunology 28(415):489-498 (1991); Studnicka et al., Protein Engineering 7(6):805-814 (1994); Roguska. et al., PNAS 91:969-973 (1994)). Examples of methods to generate fully human antibodies include, but are not limited to, generation of antibodies from mice that can express human immunoglobulin genes and use of phage-display technology to generate and screen human immunoglobulin gene libraries.

An "isolated antibody" is intended to refer to an antibody that is substantially free of other antibodies having different antigenic specificities (e.g., an isolated antibody that specifically binds CKB or SLC6a8 is substantially free of antibodies that specifically bind antigens other than such an antigen). Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM or IgG1) that is encoded by the heavy chain constant region genes. The phrases "an antibody recognizing an antigen" and "an antibody specific for an antigen" are used interchangeably herein with the term "an antibody which binds specifically to an antigen." As used herein, the term "high affinity" for an IgG antibody refers to an antibody having a $K_D$ of $10^{-7}$ M or less, preferably $10^{-8}$ M or less, more preferably $10^{-9}$ M or less and even more preferably $10^{-10}$ M or less for a target antigen. However, "high affinity" binding can vary for other antibody isotypes. For example, "high affinity" binding for an IgM isotype refers to an antibody having a $K_D$ of $10^{-7}$ M or less, more preferably $10^{-8}$ M or less.

In one example, a composition contains a monoclonal antibody that neutralizes CKB or SLC6a8. In one embodiment, this antibody can be a fully human antibody, a humanized antibody, or a non-human antibody, for example, but not limited to, a rodent (mouse or rat), goat, primate (for example, but not limited to, monkey), rabbit, or camel antibody. In one embodiment, one or more amino-acids of this monoclonal antibody may be substituted in order to alter its physical properties. These properties include, but are not limited to, binding specificity, binding affinity, immunogenicity, and antibody isotype. Pharmaceutical compositions containing fully human or humanized versions of the above described antibodies can be used for treating colon cancer or for inhibiting cancer cell survival, hypoxic survival, metastatic survival, or metastatic colonization.

As used herein, a "subject" refers to a human and a non-human animal. Examples of a non-human animal include all vertebrates, e.g., mammals, such as non-human mammals, non-human primates (particularly higher primates), dog, rodent (e.g., mouse or rat), guinea pig, cat, and rabbit, and non-mammals, such as birds, amphibians, reptiles, etc. In one embodiment, the subject is a human. In another embodiment, the subject is an experimental animal or animal suitable as a disease model. A subject to be treated for a disorder can be identified by standard diagnosing techniques for the disorder. Optionally, the subject can be examined for mutation, expression level, or activity level of one or more of CKB, SLC6a8, miR-483-5p and miR-551a mentioned above by methods known in the art or described above before treatment. If the subject has a particular mutation in the gene, or if the gene expression or activity level is, for example, greater (in the case for CKB or SLC6a8) in a sample from the subject than that in a sample from a normal person, the subject is a candidate for treatment of this invention.

To confirm the inhibition or treatment, one can evaluate and/or verify the inhibition of cancer cell survival, hypoxic survival, metastatic survival, or metastatic colonization using technology known in the art before and/or after the administering step. Exemplary technologies include CT-scans or PET-scans of organs of the body.

"Treating" or "treatment" as used herein refers to administration of a compound or agent to a subject who has a disorder with the purpose to cure, alleviate, relieve, remedy, delay the onset of, prevent, or ameliorate the disorder, the symptom of a disorder, the disease state secondary to the disorder, or the predisposition toward the disorder. An "effective amount" or "therapeutically effective amount" refers to an amount of the compound or agent that is capable of producing a medically desirable result in a treated subject. The treatment method can be performed in vivo or ex vivo, alone or in conjunction with other drugs or therapy. A therapeutically effective amount can be administered in one or more administrations, applications or dosages and is not intended to be limited to a particular formulation or administration route.

A therapeutic agent can be administered in vivo or ex vivo, alone or co-administered in conjunction with other drugs or therapy, i.e., a cocktail therapy. As used herein, the term "co-administration" or "co-administered" refers to the administration of at least two agent(s) or therapies to a subject. For example, in the treatment of tumors, particularly malignant tumors, the agents can be used alone or in combination with, e.g., chemotherapeutic, radiotherapeutic, apoptopic, anti-angiogenic agents and/or immunotoxins or coaguligands. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary.

In an in vivo approach, a compound or agent is administered to a subject. Generally, the compound is suspended in a pharmaceutically-acceptable carrier (such as, for example, but not limited to, physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily.

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100 mg/kg. Variations in the needed dosage are to be expected in view of the variety of compounds available and the different efficiencies of various routes of administration. For example, oral administration would be expected to require higher dosages than administration by i.v. injection. Variations in these dosage levels can be adjusted using standard empirical routines for optimization as is well understood in the art. Encapsulation of the compound in a suitable delivery vehicle (e.g., polymeric microparticles or implantable devices) can increase the efficiency of delivery, particularly for oral delivery.

Compositions

Within the scope of this invention is a composition that contains a suitable carrier and one or more of the therapeutic agents described above. The composition can be a pharmaceutical composition that contains a pharmaceutically acceptable carrier, a dietary composition that contains a dietarily acceptable suitable carrier, or a cosmetic composition that contains a cosmetically acceptable carrier.

The term "pharmaceutical composition" refers to the combination of an active agent with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active compound. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, sodium lauryl sulfate, and D&C Yellow #10.

The above-described composition, in any of the forms described above, can be used for treating colon cancer. An effective amount refers to the amount of an active compound/agent that is required to confer a therapeutic effect on a treated subject. Effective doses will vary, as recognized by those skilled in the art, depending on the types of diseases treated, route of administration, excipient usage, and the possibility of co-usage with other therapeutic treatment.

A pharmaceutical composition of this invention can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent. Such solutions include, but are not limited to, 1,3-butanediol, mannitol, water, Ringer's solution, and isotonic sodium chloride solution.

In addition, fixed oils are conventionally employed as a solvent or suspending medium (e.g., synthetic mono- or diglycerides). Fatty acid, such as, but not limited to, oleic acid and its glyceride derivatives, are useful in the preparation of injectables, as are natural pharmaceutically acceptable oils, such as, but not limited to, olive oil or castor oil, polyoxyethylated versions thereof. These oil solutions or suspensions also can contain a long chain alcohol diluent or dispersant such as, but not limited to, carboxymethyl cellulose, or similar dispersing agents. Other commonly used surfactants, such as, but not limited to, Tweens or Spans or other similar emulsifying agents or bioavailability enhancers, which are commonly used in the manufacture of pharmaceutically acceptable solid, liquid, or other dosage forms also can be used for the purpose of formulation.

A composition for oral administration can be any orally acceptable dosage form including capsules, tablets, emulsions and aqueous suspensions, dispersions, and solutions. In the case of tablets, commonly used carriers include, but are not limited to, lactose and corn starch. Lubricating agents, such as, but not limited to, magnesium stearate, also are typically added. For oral administration in a capsule form, useful diluents include, but are not limited to, lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

Pharmaceutical compositions for topical administration according to the described invention can be formulated as solutions, ointments, creams, suspensions, lotions, powders, pastes, gels, sprays, aerosols, or oils. Alternatively, topical formulations can be in the form of patches or dressings impregnated with active ingredient(s), which can optionally comprise one or more excipients or diluents. In some preferred embodiments, the topical formulations include a material that would enhance absorption or penetration of the active agent(s) through the skin or other affected areas.

A topical composition contains a safe and effective amount of a dermatologically acceptable carrier suitable for application to the skin. A "cosmetically acceptable" or "dermatologically-acceptable" composition or component refers a composition or component that is suitable for use in contact with human skin without undue toxicity, incompatibility, instability, allergic response, and the like. The carrier enables an active agent and optional component to be delivered to the skin at an appropriate concentration(s). The carrier thus can act as a diluent, dispersant, solvent, or the like to ensure that the active materials are applied to and distributed evenly over the selected target at an appropriate concentration. The carrier can be solid, semi-solid, or liquid. The carrier can be in the form of a lotion, a cream, or a gel, in particular one that has a sufficient thickness or yield point to prevent the active materials from sedimenting. The carrier can be inert or possess dermatological benefits. It also should be physically and chemically compatible with the active components described herein, and should not unduly impair stability, efficacy, or other use benefits associated with the composition.

Diagnosis and Prognosis Methods

The above-describe genes can be used in determining whether a subject has, or is at risk of having, metastatic colon cancer. Alternatively, they can be used for determining a prognosis of such a disorder in a subject.

Diagnosis Methods

In one aspect, the invention provides qualitative and quantitative information to determine whether a subject has or is predisposed to metastatic colon cancer, predisposed to recurrence of metastatic colon cancer, predisposed to a colon cancer that is resistant to chemotherapy, or other disease characterized by cancer cell survival, hypoxic survival, metastatic survival, or metastatic colonization. A subject having such a disorder or prone to it can be determined based on the expression levels, patterns, or profiles of the above-described genes or their products (mRNAs, microRNAs, or polypeptides) in a test sample from the subject. In other words, the products can be used as markers to indicate the presence or absence of the disorder. Diagnostic and prognostic assays of the invention include methods for assessing the expression level of the products. The methods allow one to detect the disorder. For example, a relative increase in the expression level of one or more promoters (i.e., CKB or SLC6a8) is indicative of presence the disorder. Conversely, a lower expression level or a lack of the expression is indicative lack of the disorder. Similarly, a lower expression level or a lack of one or more suppressors (i.e., miR-483-5p or miR-551a) is indicative of presence the disorder, while a relative increase in the expression level is indicative lack of the disorder.

The presence, level, or absence of, an mRNA, microRNA, or polypeptide product in a test sample can be evaluated by obtaining a test sample from a test subject and contacting the test sample with a compound or an agent capable of detecting the nucleic acid (e.g., RNA or DNA probe) or polypeptide. The "test sample" includes tissues, cells and biological fluids isolated from a subject, as well as tissues, cells and fluids present within a subject. The level of expression of a gene(s) of interest can be measured in a number of ways, including measuring the RNA encoded by the gene.

Expressed RNA samples can be isolated from biological samples using any of a number of well-known procedures. For example, biological samples can be lysed in a guanidinium-based lysis buffer, optionally containing additional components to stabilize the RNA. In some embodiments, the lysis buffer can contain purified RNAs as controls to monitor recovery and stability of RNA from cell cultures. Examples of such purified RNA templates include the Kanamycin Positive Control RNA from PROMEGA (Madison, Wis.), and 7.5 kb Poly(A)-Tailed RNA from LIFE TECHNOLOGIES (Rockville, Md.). Lysates may be used immediately or stored frozen at, e.g., $-80°$ C.

Optionally, total RNA can be purified from cell lysates (or other types of samples) using silica-based isolation in an automation-compatible, 96-well format, such as the RNEASY purification platform (QIAGEN, Inc., Valencia, Calif.). Other RNA isolation methods are contemplated, such as extraction with silica-coated beads or guanidinium. Further methods for RNA isolation and preparation can be devised by one skilled in the art.

The methods of the present invention can be performed using crude samples (e.g., blood, serum, plasma, or cell lysates), eliminating the need to isolate RNA. RNAse inhibitors are optionally added to the crude samples. When using crude cellular lysates, it should be noted that genomic DNA can contribute one or more copies of a target sequence, e.g., a gene, depending on the sample. In situations in which the target sequence is derived from one or more highly expressed genes, the signal arising from genomic DNA may not be significant. But for genes expressed at low levels, the background can be eliminated by treating the samples with DNAse, or by using primers that target splice junctions for subsequent priming of cDNA or amplification products.

The level of RNA corresponding to a gene in a cell can be determined both in situ and in vitro. RNA isolated from a test sample can be used in hybridization or amplification assays that include, Southern or Northern analyses, PCR analyses, and probe arrays. A preferred diagnostic method for the detection of RNA levels involves contacting the isolated RNA with a nucleic acid probe that can hybridize to the RNA encoded by the gene. The probe can be a full-length nucleic acid or a portion thereof, such as an oligonucleotide of at least 10 nucleotides in length and sufficient to specifically hybridize under stringent conditions to the RNA.

In one format, RNA (or cDNA prepared from it) is immobilized on a surface and contacted with the probes, for example, by running the isolated RNA on an agarose gel and transferring the RNA from the gel to a membrane, such as nitrocellulose. In another format, the probes are immobilized on a surface and the RNA (or cDNA) is contacted with the probes, for example, in a gene chip array. A skilled artisan can adapt known RNA detection methods for detecting the level of RNA.

The level of RNA (or cDNA prepared from it) in a sample encoded by a gene to be examined can be evaluated with nucleic acid amplification, e.g., by standard PCR (U.S. Pat. No. 4,683,202), RT-PCR (Bustin S. J Mol Endocrinol. 25:169-93, 2000), quantitative PCR (Ong Y. et al., Hematology. 7:59-67, 2002), real time PCR (Ginzinger D. Exp Hematol. 30:503-12, 2002), and in situ PCR (Thaker V. Methods Mol Biol. 115:379-402, 1999), or any other nucleic acid amplification method, followed by the detection of the amplified molecules using techniques known in the art. In another embodiment, the methods of the invention further include contacting a control sample with a compound or agent capable of detecting the RNA of a gene and comparing the presence of the RNA in the control sample with the presence of the RNA in the test sample.

The above-described methods and markers can be used to assess the risk of a subject for developing colon cancer. In particular, the invention can be applied to those in high risk cohort who already have certain risks so as to gain critical insight into early detection. A change in levels of the above-mentioned gene products associated with colon cancer can be detected prior to, or in the early stages of, the development of transformed or neoplastic phenotypes in cells of a subject. The invention therefore also provides a method for screening a subject who is at risk of developing colon cancer or a metastatic recurrence of their colon cancer, comprising evaluating the level of at least one gene product, or a combination of gene products, associated with the disorder in a biological sample obtained form the subject. Accordingly, an alteration in the level of the gene product, or combination of gene products, in the biological sample as compared to the level of a corresponding gene product in a control sample, is indicative of the subject being at risk for developing the disorder. The biological sample used for such screening can include a tissue sample that is either normal or suspected to be cancerous. Subjects with a change in the level of one or more gene products associated with colon cancer are candidates for further monitoring and testing. Such further testing can comprise histological examination of tissue samples, or other techniques within the skill in the art.

As used herein, the term "diagnosis" means detecting a disease or disorder or determining the stage or degree of a disease or disorder. Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease; i.e. there may be differential diagnoses that can be inferred from a diagnostic factor or symptom. Likewise, there may be instances where a factor or symptom that is indicative of a particular disease is present in an individual that does not have the particular disease. The diagnostic methods may be used independently, or in combination with other diagnosing and/or staging methods known in the medical art for a particular disease or disorder, e.g., colon cancer.

Prognosis Methods

The diagnostic methods described above can identify subjects having, or at risk of developing, colon cancer or the recurrence of metastatic colon cancer. In addition, changes in expression levels and/or trends of the above-mentioned genes in a biological sample, e.g., peripheral blood samples, can provide an early indication of recovery or lack thereof. For example, a further increase (or decline) or persistently-altered gene expression levels of the promoter genes (or inhibitor genes) indicate a poor prognosis, i.e., lack of improvement or health decline (or also a poor prognosis). Accordingly, these genes allow one to assess post-treatment recovery of colon cancer. The analysis of this select group of genes or a subset thereof indicates outcomes of the conditions.

The prognostic assays described herein can be used to determine whether a subject is suitable to be administered with an agent (e.g., an agonist, antagonist, peptidomimetic, protein, peptide, nucleic acid, small molecule, or other drug candidate) to treat colon cancer or other disorders associated with cancer cell survival, hypoxic survival, metastatic survival, or metastatic colonization. For example, such assays can be used to determine whether a subject can be administered with a chemotherapeutic agent.

Thus, also provided by this invention is a method of monitoring a treatment for a cellular proliferative disorder in a subject. For this purpose, gene expression levels of the genes disclosed herein can be determined for test samples from a subject before, during, or after undergoing a treatment. The magnitudes of the changes in the levels as compared to a baseline level are then assessed. A decrease in the expression of the above-mentioned promoter genes (e.g., CKB or SLC6a8) after the treatment indicates that the subject can be further treated by the same treatment. Similarly, an increase in the inhibitors (e.g., miR-483-5p or miR-551a) also indicates that the subject can be further treated by the same treatment. Conversely, further increase or persistent high expression levels of one or more of the promoter genes (or further decrease or persistent low or no expression levels of one or more of the inhibitors genes) indicates lack of improvement or health decline.

Information obtained from practice of the above assays is useful in prognostication, identifying progression of, and clinical management of diseases and other deleterious conditions affecting an individual subject's health status. In preferred embodiments, the foregoing diagnostic assays provide information useful in prognostication, identifying progression of and management of colon cancer, metastatic colon cancer and other conditions characterized by cancer cell survival, hypoxic survival, metastatic survival, or metastatic colonization. The information more specifically assists the clinician in designing chemotherapeutic or other treatment regimes to eradicate such conditions from the body of an afflicted subject, a human.

The term "prognosis" as used herein refers to a prediction of the probable course and outcome of a clinical condition or disease. A prognosis is usually made by evaluating factors or symptoms of a disease that are indicative of a favorable or unfavorable course or outcome of the disease. The phrase "determining the prognosis" as used herein refers to the process by which the skilled artisan can predict the course or outcome of a condition in a patient. The term "prognosis" does not refer to the ability to predict the course or outcome of a condition with 100% accuracy instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition.

The terms "favorable prognosis" and "positive prognosis," or "unfavorable prognosis" and "negative prognosis" as used herein are relative terms for the prediction of the probable course and/or likely outcome of a condition or a disease. A favorable or positive prognosis predicts a better outcome for a condition than an unfavorable or negative prognosis. In a general sense, a "favorable prognosis" is an outcome that is relatively better than many other possible prognoses that could be associated with a particular condition, whereas an unfavorable prognosis predicts an outcome that is relatively worse than many other possible prognoses that could be associated with a particular condition. Typical examples of a favorable or positive prognosis include a better than average cure rate, a lower propensity for metastasis, a longer than expected life expectancy, differentiation of a benign process from a cancerous process, and the like. For example, a positive prognosis is one where a patient has a 50% probability of being cured of a particular cancer after treatment, while the average patient with the same cancer has only a 25% probability of being cured.

The terms "determining," "measuring," "assessing," and "assaying" are used interchangeably and include both quantitative and qualitative measurement, and include determining if a characteristic, trait, or feature is present or not. Assessing may be relative or absolute. "Assessing the presence of" a target includes determining the amount of the target present, as well as determining whether it is present or absent.

Arrays

Also provided in the invention is a biochip or array. The biochip/array may contain a solid or semi-solid substrate having an attached probe or plurality of probes described herein. The probes may be capable of hybridizing to a target sequence under stringent hybridization conditions. The probes may be attached at spatially defined address on the substrate. More than one probe per target sequence may be used, with either overlapping probes or probes to different sections of a particular target sequence. The probes may be capable of hybridizing to target sequences associated with a single disorder appreciated by those in the art. The probes may either be synthesized first, with subsequent attachment to the biochip, or may be directly synthesized on the biochip.

"Attached" or "immobilized" as used herein to refer to a nucleic acid (e.g., a probe) and a solid support may mean that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

The solid substrate can be a material that may be modified to contain discrete individual sites appropriate for the attachment or association of the probes and is amenable to at least one detection method. Examples of such substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate can be planar, although other configurations of substrates may be used as well. For example, probes may be placed on the inside surface of a tube, for flow-through sample analysis to minimize sample volume. Similarly, the substrate may be flexible, such as flexible foam, including closed cell foams made of particular plastics.

The array/biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the solid support by either the 5' terminus, 3' terminus, or via an internal nucleotide. The probe may also be attached to the solid support non-covalently. For example, biotinylated oligonucleotides can be made, which may bind to surfaces covalently coated with streptavidin, resulting in attachment.

Alternatively, probes may be synthesized on the surface using techniques such as photopolymerization and photolithography. Detailed discussion of methods for linking nucleic acids to a support substrate can be found in, e.g., U.S. Pat. Nos. 5,837,832, 6,087,112, 5,215,882, 5,707,807, 5,807,522, 5,958,342, 5,994,076, 6,004,755, 6,048,695, 6,060,240, 6,090,556, and 6,040,138.

In some embodiments, an expressed transcript (e.g., a transcript of a microRNA or polypeptide gene described herein) is represented in the nucleic acid arrays. In such embodiments, a set of binding sites can include probes with different nucleic acids that are complementary to different sequence segments of the expressed transcript. Examples of such nucleic acids can be of length of 15 to 200 bases, 20 to 100 bases, 25 to 50 bases, 40 to 60 bases. Each probe sequence can also include one or more linker sequences in addition to the sequence that is complementary to its target sequence. A linker sequence is a sequence between the sequence that is complementary to its target sequence and the surface of support. For example, the nucleic acid arrays of the invention can have one probe specific to each target microRNA gene. However, if desired, the nucleic acid arrays can contain at least 2, 5, 10, 100, 200, 300, 400, 500 or more probes specific to some expressed transcript (e.g., a transcript of a microRNA gene described herein).

Kits

In another aspect, the present invention provides kits embodying the methods, compositions, and systems for analysis of the polypeptides and microRNA expression as described herein. Such a kit may contain a nucleic acid described herein together with any or all of the following: assay reagents, buffers, probes and/or primers, and sterile saline or another pharmaceutically acceptable emulsion and suspension base. In addition, the kit may include instructional materials containing directions (e.g., protocols) for the practice of the methods described herein. For example, the kit may be a kit for the amplification, detection, identification or quantification of a target mRNA or microRNA sequence. To that end, the kit may contain a suitable primer (e.g., hairpin primers), a forward primer, a reverse primer, and a probe.

In one example, a kit of the invention includes one or more microarray slides (or alternative microarray format) onto which a plurality of different nucleic acids (each corresponding to one of the above-mentioned genes) have been deposited. The kit can also include a plurality of labeled probes. Alternatively, the kit can include a plurality of polynucleotide sequences suitable as probes and a selection of labels suitable for customizing the included polynucleotide sequences, or other polynucleotide sequences at the discretion of the practitioner. Commonly, at least one included polynucleotide sequence corresponds to a control sequence, e.g., a normalization gene or the like. Exemplary labels include, but are not limited to, a fluorophore, a dye, a radiolabel, an enzyme tag, that is linked to a nucleic acid primer.

In one embodiment, kits that are suitable for amplifying nucleic acid corresponding to the expressed RNA samples are provided. Such a kit includes reagents and primers suitable for use in any of the amplification methods described above. Alternatively, or additionally, the kits are suitable for amplifying a signal corresponding to hybridization between a probe and a target nucleic acid sample (e.g., deposited on a microarray).

In addition, one or more materials and/or reagents required for preparing a biological sample for gene expression analysis are optionally included in the kit. Furthermore, optionally included in the kits are one or more enzymes suitable for amplifying nucleic acids, including various polymerases (RT, Taq, etc.), one or more deoxynucleotides, and buffers to provide the necessary reaction mixture for amplification.

Typically, the kits are employed for analyzing gene expression patterns using mRNA or microRNA as the starting template. The RNA template may be presented as either total cellular RNA or isolated RNA; both types of sample yield comparable results. In other embodiments, the methods and kits described in the present invention allow quantitation of other products of gene expression, including tRNA, rRNA, or other transcription products.

Optionally, the kits of the invention further include software to expedite the generation, analysis and/or storage of data, and to facilitate access to databases. The software includes logical instructions, instructions sets, or suitable computer programs that can be used in the collection, storage and/or analysis of the data. Comparative and relational analysis of the data is possible using the software provided.

The kits optionally contain distinct containers for each individual reagent and/or enzyme component. Each component will generally be suitable as aliquoted in its respective container. The container of the kits optionally includes at least one vial, ampule, or test tube. Flasks, bottles and other container mechanisms into which the reagents can be placed and/or aliquoted are also possible. The individual containers of the kit are preferably maintained in close confinement for commercial sale. Suitable larger containers may include injection or blow-molded plastic containers into which the desired vials are retained. Instructions, such as written directions or videotaped demonstrations detailing the use of the kits of the present invention, are optionally provided with the kit.

In a further aspect, the present invention provides for the use of any composition or kit herein, for the practice of any method or assay herein, and/or for the use of any apparatus or kit to practice any assay or method herein.

A "test sample" or a "biological sample" as used herein may mean a sample of biological tissue or fluid that comprises nucleic acids. Such samples include, but are not limited to, tissue or body fluid isolated from animals. Biological samples may also include sections of tissues such as biopsy and autopsy samples, frozen sections taken for histological purposes, blood, plasma, serum, sputum, stool, tears, mucus, urine, effusions, amniotic fluid, ascitic fluid, hair, and skin. Biological samples also include explants and primary and/or transformed cell cultures derived from patient tissues. A biological sample may be provided by removing a sample of cells from an animal, but can also be accomplished by using previously isolated cells (e.g., isolated by another person, at another time, and/or for another purpose), or by performing the methods described herein in vivo. Archival tissues, such as those having treatment or outcome history, may also be used.

The term "body fluid" or "bodily fluid" refers to any fluid from the body of an animal. Examples of body fluids include, but are not limited to, plasma, serum, blood, lymphatic fluid, cerebrospinal fluid, synovial fluid, urine, saliva, mucous, phlegm and sputum. A body fluid sample may be collected by any suitable method. The body fluid sample may be used immediately or may be stored for later use. Any suitable storage method known in the art may be used to store the body fluid sample: for example, the sample may be frozen at about −20° C. to about −70° C. Suitable body fluids are acellular fluids. "Acellular" fluids include body fluid samples in which cells are absent or are present in such low amounts that the miRNA level determined reflects its level in the liquid portion of the sample, rather than in the cellular portion. Such acellular body fluids are generally produced by processing a cell-containing body fluid by, for example, centrifugation or filtration, to remove the cells. Typically, an acellular body fluid contains no intact cells however, some may contain cell fragments or cellular debris. Examples of acellular fluids include plasma or serum, or body fluids from which cells have been removed.

The term "gene" used herein refers to a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto. The term also includes pseudogenes, which are dysfunctional relatives of known genes that have lost their protein-coding ability or are otherwise no longer expressed in a cell.

"Expression profile" as used herein refers to a genomic expression profile, e.g., an expression profile of microRNAs. Profiles may be generated by any convenient means for determining a level of a nucleic acid sequence e.g., quantitative hybridization of microRNA, cRNA, etc., quantitative PCR, ELISA for quantification, and the like, and allow the analysis of differential gene expression between two samples. A subject or patient sample, e.g., cells or a collection thereof, e.g., tissues, is assayed. Samples are collected by any convenient method, as known in the art. Nucleic acid sequences of interest are nucleic acid sequences that are found to be predictive, including the nucleic acid sequences of those described herein, where the expression profile may include expression data for 5, 10, 20, 25, 50, 100 or more of, including all of the listed nucleic acid sequences. The term "expression profile" may also mean measuring the abundance of the nucleic acid sequences in the measured samples.

"Differential expression" refers to qualitative or quantitative differences in the temporal and/or cellular gene expression patterns within and among cells and tissue. Thus, a differentially expressed gene can qualitatively have its expression altered, including an activation or inactivation, in, e.g., normal versus disease tissue. Genes may be turned on or turned off in a particular state, relative to another state thus permitting comparison of two or more states. A qualitatively regulated gene will exhibit an expression pattern within a state or cell type that may be detectable by standard techniques. Some genes will be expressed in one state or cell type, but not in both. Alternatively, the difference in expression may be quantitative, e.g., in that expression is modulated, up-regulated, resulting in an increased amount of transcript, or down-regulated, resulting in a decreased amount of transcript. The degree to which expression differs need only be large enough to quantify via standard characterization techniques such as expression arrays, quantitative reverse transcriptase PCR, Northern analysis, and RNase protection.

"Nucleic acid" or "oligonucleotide" or "polynucleotide" as used herein refers to at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

The term "primer" refers to any nucleic acid that is capable of hybridizing at its 3' end to a complementary nucleic acid molecule, and that provides a free 3' hydroxyl terminus which can be extended by a nucleic acid polymerase. As used herein, amplification primers are a pair of nucleic acid molecules that can anneal to 5' or 3' regions of a gene (plus and minus strands, respectively, or vice-versa) and contain a short region in between. Under appropriate conditions and with appropriate reagents, such primers permit the amplification of a nucleic acid molecule having the nucleotide sequence flanked by the primers. For in situ methods, a cell or tissue sample can be prepared and immobilized on a support, such as a glass slide, and then contacted with a probe that can hybridize to RNA. Alternative methods for amplifying nucleic acids corresponding to expressed RNA samples include those described in, e.g., U.S. Pat. No. 7,897,750.

The term "probe" as used herein refers to an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

"Complement" or "complementary" as used herein to refer to a nucleic acid may mean Watson-Crick (e.g., A-T/U and C-G) or Hoogsteen base pairing between nucleotides or nucleotide analogs of nucleic acid molecules. A full complement or fully complementary may mean 100% complementary base pairing between nucleotides or nucleotide analogs of nucleic acid molecules.

"Stringent hybridization conditions" as used herein refers to conditions under which a first nucleic acid sequence (e.g., probe) hybridizes to a second nucleic acid sequence (e.g., target), such as in a complex mixture of nucleic acids. Stringent conditions are sequence-dependent and be different in different circumstances, and can be suitably selected by one skilled in the art. Stringent conditions may be selected to be about 5-10° C. lower than the thermal melting point (Tm) for the specific sequence at a defined ionic strength pH. The Tm may be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C. However, several factors other than temperature, such as salt concentration, can influence the stringency of hybridization and one skilled in the art can suitably select the factors to accomplish a similar stringency.

As used herein the term "reference value" refers to a value that statistically correlates to a particular outcome when compared to an assay result. In preferred embodiments, the reference value is determined from statistical analysis of studies that compare microRNA or protein expression with known clinical outcomes. The reference value may be a threshold score value or a cutoff score value. Typically a reference value will be a threshold above (or below) which one outcome is more probable and below which an alternative threshold is more probable.

In one embodiment, a reference level may be one or more miRNA or polypeptide levels expressed as an average of the level of the miRNA or polypeptide from samples taken from a control population of healthy (disease-free) subjects. In another embodiment, the reference level may be the level in the same subject at a different time, e.g., before the present assay, such as the level determined prior to the subject developing the disease or prior to initiating therapy. In general, samples are normalized by a common factor. For example, acellular body fluid samples are normalized by volume body fluid and cell-containing samples are normalized by protein content or cell count. Nucleic acid samples may also be normalized relative to an internal control nucleic acid.

As disclosed herein, the difference of the level of one or more polypeptides or RNAs (mRNAs or microRNAs) is indicative of a disease or a stage thereof. The phrase "difference of the level" refers to differences in the quantity of a particular marker, such as a nucleic acid, in a sample as compared to a control or reference level. For example, the quantity of a particular biomarker may be present at an elevated amount or at a decreased amount in samples of patients with a neoplastic disease compared to a reference level. In one embodiment, a "difference of a level" may be a difference between the quantity of a particular biomarker present in a sample as compared to a control (e.g., reference value) of at least about 1%, 2%, 3%, 5%, 10%, 15%, 20%, 25%, 30%, 35%, 40%, 50%, 60%, 75%, 80% 100%, 150%, 200%, or more. In one embodiment, a "difference of a level" may be a statistically significant difference between the quantities of a biomarker present in a sample as compared to a control. For example, a difference may be statistically significant if the measured level of the biomarker falls outside of about 1.0 standard deviation, about 1.5 standard deviations, about 2.0 standard deviations, or about 2.5 stand deviations of the mean of any control or reference group. With respect to miRNA measurement, the level may be measured from real-time PCR as the Ct value, which may be normalized to a ΔCt value as described in the Examples below.

Drug Screening

The invention provides a method for identifying a compound that is useful for treating colon cancer or for inhibiting cancer cell survival, hypoxic survival, metastatic survival, or metastatic colonization.

Candidate compounds to be screened (e.g., proteins, peptides, peptidomimetics, peptoids, antibodies, small molecules, or other drugs) can be obtained using any of the numerous approaches in combinatorial library methods known in the art. Such libraries include: peptide libraries, peptoid libraries (libraries of molecules having the functionalities of peptides, but with a novel, non-peptide backbone that is resistant to enzymatic degradation); spatially addressable parallel solid phase or solution phase libraries; synthetic libraries obtained by deconvolution or affinity chromatography selection; and the "one-bead one-compound" libraries. See, e.g., Zuckermann et al. 1994, J. Med. Chem. 37:2678-2685; and Lam, 1997, Anticancer Drug Des. 12:145. Examples of methods for the synthesis of molecular libraries can be found in, e.g., DeWitt et al., 1993, PNAS USA 90:6909; Erb et al., 1994, PNAS USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994 J. Med. Chem. 37:1233. Libraries of compounds may be presented in solution (e.g., Houghten, 1992, Biotechniques 13:412-421), or on beads (Lam, 1991, Nature 354:82-84), chips (Fodor, 1993, Nature 364:555-556), bacteria (U.S. Pat. No. 5,223,409), spores (U.S. Pat. No. 5,223,409), plasmids (Cull et al., 1992, PNAS USA 89:1865-1869), or phages (Scott and Smith 1990, Science 249:386-390; Devlin, 1990, Science 249:404-406; Cwirla et al., 1990, PNAS USA 87:6378-6382; Felici 1991, J. Mol. Biol. 222:301-310; and U.S. Pat. No. 5,223,409).

To identify a useful compound, one can contact a test compound with a system containing test cells expressing a reporter gene encoded by a nucleic acid operatively liked to a promoter of a marker gene selected from the above-mentioned metastasis promoters or suppressors. The system can be an in vitro cell line model or an in vivo animal model. The cells can naturally express the gene, or can be modified to express a recombinant nucleic acid. The recombinant nucleic acid can contain a nucleic acid coding a reporter polypeptide to a heterologous promoter. One then measures the expression level of the miRNA, polypeptide, or reporter polypeptide.

For the polypeptide, the expression level can be determined at either the mRNA level or at the protein level. Methods of measuring mRNA levels in a cell, a tissue sample, or a body fluid are well known in the art. To measure mRNA levels, cells can be lysed and the levels of mRNA in the lysates or in RNA purified or semi-purified from the lysates can be determined by, e.g., hybridization assays (using detectably labeled gene-specific DNA or RNA probes) and quantitative or semi-quantitative RT-PCR (using appropriate gene-specific primers). Alternatively, quantitative or semi-quantitative in situ hybridization assays can be carried out using tissue sections or unlysed cell suspensions, and detectably (e.g., fluorescent or enzyme) labeled DNA or RNA probes. Additional mRNA-quantifying methods include RNA protection assay (RPA) and SAGE. Methods of measuring protein levels in a cell or a tissue sample are also known in the art.

To determine the effectiveness of a candidate compound to treat colon cancer or inhibiting cancer cell survival, hypoxic survival, metastatic survival, or metastatic colonization, one can compare the level obtained in the manner described above with a control level (e.g., one obtained in the absence of the candidate compound). The compound is identified as being effective if (i) a metastasis suppressor's level is higher than a control or reference value or (ii) a metastasis promoter's level is lower than the control or reference value. One can further verify the efficacy of a compound thus-identified using the in vitro cell culture model or an in vivo animal model as disclosed in the example below.

EXAMPLE 1

This example describes materials and methods used in EXAMPLES 2-15 below.

In Vivo Selection $1 \times 10^6$ LS 174T cells expressing a luciferase reporter were suspended in a volume of 20 μl 1:1 PBS/Matrigel mixture and injected intra-hepatically into the livers of NOD-SCID mice. Metastatic nodules were allowed to develop over a period of 3-4 weeks and monitored by bioluminescence imaging. Nodules formed were excised and dissociated by collagenase and hyaluronidase digestion into single cell suspension. The cells were allowed to expand in in vitro before re-injection into mice. After three re-iterations of in vivo selection, highly metastatic LvM3a and LvM3b derivative cell-lines were established.

Lenti-miR Library Screening

Cells were transduced with a lentivirus Lenti-miR library of 611 miRNAs (System Biosciences) at a low multiplicity of infection (MOI) such that each cell over-expressed a single miRNA. The transduced population was then injected intra-hepatically into NOD-SCID mice for in vivo selection of miRNAs that when over-expressed, either promoted or suppressed metastatic liver colonization. Genomic DNA PCR amplification and recovery of lenti-viral miRNA inserts were performed on cells prior to injection and from liver nodules according to manufacturer's protocol. miRNA array profiling allowed for miRNA insert quantification prior to and after in vivo selection.

Organotypic Slice Culture System

Cells to be injected were labeled with cell-tracker red or green (Invitrogen) and inoculated into livers of NOD-SCID mice through intrasplenic injection. The livers were then extracted and cut into 150 um slices using a McIlwain tissue chopper (Ted Pella) and plated onto organotypic tissue culture inserts (Millipore) and cultured in William's E Medium supplemented with Hepatocyte Maintenance Supplement Pack (Invitrogen). After indicated time periods, the liver slices were fixed in paraformaldehyde and imaged using multi-photon microscopy.

In Vivo Caspase Activation Assay

To measure caspase activity in vivo, VivoGlo Caspase 3/7 Substrate (Z-DEVD-Aminoluciferin Sodium Salt, Promega) was used. The luciferin is inactive until the DEVD peptide is cleaved from by activated caspase-3 in apoptotic cells. DEVD-luciferin was injected into mice bearing colorectal cancer cells expressing luciferase. Upon activation by apoptotic cells, bioluminescence imaging can be performed to measure caspase activity in vivo. Five hours after in vivo caspase activity measurement, mice are injected with regular luciferin for normalization purposes.

Adeno-Associated Viral Therapy miR-483-5p and miR-551a were cloned as a polycistron consisting of both miRNA precursor with flanking genomic sequences in tandem into the BglII and NotI site of scAAV.GFP (Plasmid 21893, Addgene). Listed below are genomic sequences encoding for miR-483-5p and miR-551a (SEQ ID NOs: 5 and 6), corresponding precursor sequences (underlined, SEQ ID NOs: 3 and 4), and corresponding mature microRNA sequences (underlined and in bold, SEQ ID NOs: 1 and 2). Adeno-associated viruses were packaged, purified and titered using the AAV-DJ Helper Free expression system from Cell Biolabs.

miR-551a:
GGAGAACCTTCAGCTTCATGTGACCCAGAGACTCCTGTATGCCTGGCTCT

GGGAGTACAGAAGGGCCTAGAGCTGACCCCTGCCCTCCGAAGCCCCTGGG

GCACTAGATGGATGTGTGCCAGAGGGTAGTAGAGGCCTGGGGGTAGAGCC

CAGCACCCCCTTCGCGTAGAGACCTGGGGGACCAGCCAGCCCAGCAACCC

CCTCGCGGCCGACGCCTGAGGCTGTTCCTGGCTGCTCCGGTGGCTGCCAG

A GGGGACTGCCGGGTGACCCTGGAAATCCAGAGTGGGTGGGGCCAGTCTG

ACCGTTTCTAGGCGACCCACTCTTGGTTTCCAGGGTTGCCCTGGAAACCA

CAGATGGGGAGGGGTTGATGGCACCCAGCCTCCCCCAAGCCTGGGAAGGG

ACCCCGGATCCCCAGAGCCTTTCCCTGCCTATGGAGCGTTTCTCTTGGAG

AACAGGGGGCCTCTCAGCCCCTCAATGCAAGTTGCTGAG miR-483-5p:
CCTGCCCCATTTGGGGGTAGGAAGTGGCACTGCAGGGCCTGGTGCCAGCC

AGTCCTTGCCCAGGGAGAAGCTTCCCTGCACCAGGCTTTCCTGAGAGGAG

GGGAGGGCCAAGCCCCCACTTGGGGGACCCCCGTGATGGGGCTCCTGCTC

CCTCCTCCGGCTGATGGCACCTGCCCTTTGGCACCCCAAGGTGGAGCCCC

CAGCGACCTTCCCCTTCCAGCTGAGCATTGCTGTGGGGA GAGGGG**GAAG

ACGGGAGGAAAGAAGGGAG**TGGTTCCATCACGCCTCCTCACTCCTCTCCT

CCCGTCTTCTCCTCTCCTGCCCTTGTCTCCCTGTCTCAGCAGCTCCAGG

GTGGTGTGGGCCCCTCCAGCCTCCTAGGTGGTGCCAGGCCAGAGTCCAAG

CTCAGGGACAGCAGTCCCTCCTGTGGGGGCCCCTGAACTGGGCTCACATC

CCACACATTTTCCAAACCACTCCCATTGTGAGCCTTTGGTCCTGGTGGTG

TCCCTCTGGTTGTGGGACCAAGAGCTTGTGCCCATTTTTCATCTGAGGAA

GGAGGCAGC

Listed below are the corresponding RNA sequences for SEQ ID NOs: 1-4 (SEQ ID NOs: 7-10)

(SEQ ID NO: 7)
GACCCACUCUUGGUUUCCA (SEQ ID NO: 8)
GGGGACUGCCGGGUGACCCUGGAAAUCCAGAGUGGGUGGGGCCAGUCUGA

CCGUUUCUAGGCGACCCACUCUUGGUUUCCAGGGUUGCCCUGGAAA (SEQ ID NO: 9)
GAAGACGGGAGGAAAGAAGGGAG (SEQ ID NO: 10)
GAGGGGGAAGACGGGAGGAAAGAAGGGAGUGGUUCCAUCACGCCUCCUCA

CUCCUCUCCUCCCGUCUUCUCCUCUC

CKB, SLC6a8 Knockdown pLKO vectors expressing shRNA hairpins targeting CKB and SLC6a8 were ordered from Sigma-Aldrich. Two independent hairpins that gave the best knockdown of transcript levels were used for all experiments. These hairpin DNA and RNA sequences are listed below:

| Name | DNA Sequences | SEQ ID NO | RNA Sequences | SEQ ID NO |
|---|---|---|---|---|
| CKB | CCGGCCCAGATTGAA ACTCTCTTCACTCGA GTGAAGAGAGTTTCA ATCTGGGTTTTT | 11 | CCGGCCCAGAUUGAA ACUCUCUUCACUCGA GUGAAGAGAGUUUCA AUCUGGGUUUUU | 15 |
| CKB | CCGGCCGCGGTATCT GGCACAATGACTCGA GTCATTGTGCCAGAT ACCGCGGTTTTTG | 12 | CCGGCCGCGGUAUCU GGCACAAUGACUCGA GUCAUUGUGCCAGAU ACCGCGGUUUUUG | 16 |
| shSLC6a8 #2 | CCGGGCTGGTCTACA ACAACACCTACTCGA GTAGGTGTTGTTGTA GACCAGCTTTTG | 19 | CCGGGCUGGUCUACA ACAACACCUACUCGA GUAGGUGUUGUUGUA GACCAGCUUUUUG | 20 |
| shSLC6a8 #4 | CCGGCTTATTCCCTA CGTCCTGATCCTCGA GGATCAGGACGTAGG GAATAAGTTTTG | 13 | CCGGCUUAUUCCCUA CGUCCUGAUCCUCGA GGAUCAGGACGUAGG GAAUAAGUUUUUG | 17 |
| shSLC6a8 #5 | CCGGATTACCTGGTC AAGTCCTTTACTCGA GTAAAGGACTTGACC AGGTAATTTTTG | 14 | CCGGAUUACCUGGUC AAGUCCUUUACUCGA GUAAAGGACUUGACC AGGUAAUUUUUG | 18 |

The following primers were used for quantitative qRT-PCR of SLC6a8: Forward Primer: 5'-GGC AGC TAC AAC CGC TTC AAC A-3' and Reverse Primer: 5'-CAG GAT GGA GAA GAC CAC GAA G-3' (SEQ ID No. 21 and 22, respectively).

Cyclocreatine and Beta-Guanidiopropionic Acid Treatment

Mice were treated with 10 mg of cyclocreatine or saline vehicle, administered through intra-peritoneal injection. The treatment regime started one day after inoculation of tumor cells and continued until the mice were euthanized. Beta-guanidipropionic acid was administered at a dose of 200 ul of 0.5M solution through intra-peritoneal injection. Treatment regime were as that for cyclocreatine treatment.

EXAMPLE 2

As a first step to identify molecular regulators of liver colonization by colon cancer, an in vivo selection was performed on the LS-174T human colon cancer line for enhanced liver colonization through iterative intra-hepatic injection of cancer cells into immunodeficient mice followed by surgical resection of the liver colonies and dissociation of cells. More specifically, liver colonization by $5 \times 10^5$ LS-Parental, LvM3a and LvM3b cells was examined after direct intrahepatic injection by bioluminescence. Mice were imaged at day 21 after injection and livers extracted for ex vivo imaging and gross morphological examination. Photon flux ratios for the groups were obtained and compared. It was found that third-generation liver colonizers LS-LvM3a and LS-LvM3b displayed dramatically enhanced (>50 fold) capacity for liver colonization upon intra-hepatic injection relative to their parental line. Importantly, these derivatives also displayed significantly enhanced (>150 fold) liver metastatic capacity upon portal circulation injection in metastatic colonization assays—revealing liver colonization capacity to be a key step in colon cancer metastatic progression. For these bioluminescence assays, all P values for the groups' respective photon flux ratios were based on one-sided Student's t-tests and found to be less than 0.05, 0.001, or 0.0001.

In order to systematically identify microRNA regulators of metastatic progression, a library of lentiviral particles, each encoding one of 611 human microRNAs, was transduced into the LS-LvM3b colonizer population, the LS-174T parental line, as well as the SW620 colon cancer population. These cancer populations, containing cancer cells expressing each of 661 miRNAs, were then intra-hepatically injected into mice in order to allow for the selection of cells capable of colonizing the liver. Genomic PCR amplification of miRNA sequences, reverse-transcription, and miRNA profiling of miRNA inserts allowed for the quantification of miRNA insert representation. It was identified that several miRNAs displayed drop-out in the context of liver colonization in both colon cancer cell lines, consistent with the over-expression of these miRNAs suppressing liver colonization by colon cancer cells.

EXAMPLE 3

In this example, assays were carried out to examine whether endogenous levels of any of these miRNAs exhibit silencing in highly metastatic derivatives relative to isogenic poorly metastatic cells. Indeed, miR-483-5p and miR-551a were found to be silenced in highly metastatic LS-LVM3a and LS-LVM3b liver colonizers relative to their parental line and the metastatic SW620 derivative relative to its isogenic parental line. Consistent with a suppressive role for these miRNAs in liver colonization, over-expression of miR-483-5p or miR-551a robustly suppressed metastatic colonization by the LS-LvM3b cells, while inhibition of endogenous miR-483-5p or miR-551a in poorly metastatic parental lines LS-174T and SW480 significantly enhanced liver metastatic colonization.

EXAMPLE 4

In this example, assays were carried out to investigate the mechanism(s) by which these miRNAs exert their anti-metastatic effects. The effects of these miRNAs on metastatic progression were not secondary to modulation of proliferative capacity since miR-551a inhibition did not effect in vitro proliferation, while miR-483-5p inhibition increased proliferation. Additionally, over-expression of these miRNAs did not alter the invasive capacity or apoptotic rates of cancer cells. In order to determine the mechanism(s) by which these miRNAs impact metastasis, assays were performed to identify the time-point during the metastatic process when cells over-expressing these miRNAs display a defect in progression. Surprisingly, it was noted that as early as 24 hours after injection of cells into the portal circulation for hepatic metastatic colonization assays, cells over-expressing these miRNAs were out-competed in their representation relative to cells expressing a control hairpin.

EXAMPLE 5

To elucidate the mechanism(s) by which these miRNAs suppress liver metastatic colonization, an in vitro liver organotypic slice culture system was developed. This system allowed one to study early events during liver metastasis after single-cell dissemination of colon cancer cells in the liver microenvironment. Consistent with prior studies on a significant selection on cell survival during metastatic colonization, there was a large drop-off in the numbers of cells within the liver microenvironment as a function of time. Highly metastatic LvM3b colonizer cells were significantly better at persisting in the liver microenvironment than their poorly metastatic parental line—consistent with a positive role for intrahepatic persistence in metastatic progression.

Next, assays were carried out to investigate whether the effects of this miRNA regulatory network on cancer cell persistence are caused by diminished cancer cell survival during metastatic progression. To quantify cell death in vivo, a bioluminescence-based luciferin reporter of caspace-3/7 activity was utilized.

More specifically, SW480 cells whose endogenous miR-483-5p or miR-551a were inhibited and subsequently introduced into the liver of immunodeficient mice by intrasplenic injection. Then, relative in vivo caspase activity in these cells was monitored using a caspase-3 activated DEVD-luciferin. It was found that miRNA inhibition significantly reduced in vivo caspase activity in colon cancer cells during the early phase of hepatic colonization, revealing cancer survival to be the phenotype suppressed by these miRNAs.

These in vivo findings were corroborated by an organotypic slice culture system. Briefly, survival of the SW480 cells in organotypic cultures (n=8) whose endogenous miR-483-5p or miR-551a were inhibited by pre-treatment with LNAs. $5\times10^5$ cells were labeled with cell-tracker green (LS-Parental) or cell-tracker red (LvM3b) and introduced into the liver through intrasplenic injection. Immediately after injection, the liver was excised and 150-um slice cultures were made using a tissue chopper. Survival of the cells in organotypic cultures was monitored for up to 4 days with a multi-photon microscope. Dye-swap experiments were performed to exclude effects of dye bias. Representative images at day 0 and day 3 were shown. It was found that over-expression of both microRNAs in LS-LvM3b cells suppressed colon cancer persistence while inhibition of endogenous levels of both microRNAs enhanced persistence of poorly metastatic SW480 cells. The above findings reveal miR-483-5p and miR-551a to suppress liver metastatic colonization and metastatic cell survival in the liver—a phenotype exhibited by highly metastatic colon cancer cells.

EXAMPLE 6

In this example, assays were carried out to identify the downstream effectors of these miRNAs. Through transcriptomic profiling, transcripts that were down-regulated by over-expression of each microRNA and which contained 3'-UTR or coding-sequence (CDS) elements complementary to the miRNAs were identified. Interestingly, Creatine Kinase Brain-type (CKB) was identified as a putative target of both miRNAs, suggesting that these miRNAs, which exhibit common in vivo and organotypic phenotypes might mediate their effects through a common target gene. Indeed, quantitative PCR validation revealed suppression of CKB transcript levels upon over-expression of the microRNAs. It was found that expression levels of CKB in highly metastatic LvM3b cells were suppressed by over-expressing miR-483-5p and miR-551a. Additionally, endogenous miR-483 and miR-551a were found to suppress endogenous CKB protein levels. For example, it was found that expression of CKB was up-regulated in poorly metastatic SW480 cells whose endogenous miR-483-5p and miR-551aa were inhibited with LNAs. Mutagenesis and luciferase-based reporter assays revealed miR-483-5p and miR-551a to directly target the 3'UTR or CDS of CKB. To that end, luciferase reporter assays of CKB coding sequence and 3'-UTR were carried out. It was found that miR-483-5p and miR-551a targeted complementary regions in the 3'-UTR and coding sequence of CKB respectively. The assays were performed with the complementary regions mutated as well and they were performed at least 3 times.

EXAMPLE 7

In this example, assays were carried out to examine if CKB is sufficient and necessary for liver metastatic colonization by colon cancer.

Briefly, liver metastasis was examined in mice injected intrasplenically with $5\times10^5$ poorly metastatic SW480 cells and CKB over-expressing cells. The mice were euthanized at 28 days after injection and livers excised for bioluminescent imaging. Similarly, liver metastasis was also examined in mice injected intrasplenically with $5\times10^5$ highly aggressive LvM3b expressing a control hairpin or a hairpin targeting CKB. These mice were euthanized 21 days after injection as described above.

It was found that over-expression of CKB in poorly metastatic SW480 cells was sufficient to promote liver metastasis by more than 3-folds, while CKB knockdown in metastatic LS-LvM3b cells and SW480 cells, through independent hairpin knockdown in each line robustly suppressed liver metastasis by more than 5 folds. Consistent with the effects of the miRNAs, CKB over-expression was sufficient to significantly enhance the ability of colon cancer cells to persist in the liver micro-environment and enhanced their representation in the liver, while CKB knockdown significantly reduced intra-hepatic persistence. To that end, study was carried out to examine survival of control SW480 and CKB over-expressing SW480 cells in organotypic liver slices (n=8), and organotypic slice cultures of LvM3b cells expressing a control hairpin or hairpin targeting CKB (n=8). Images taken at day 0 and day 2 showed that CKB over-expression was sufficient to significantly enhance the ability of cancer cells. In these assays, P values were found to be less than 0.001 or 0.0001 based on one-sided Student's t-tests.

To investigate whether CKB acts directly downstream of miR-483-5p and miR-551a, the coding-sequence of CKB was over-expressed in cells over-expressing miR-483-5p or miR-551a. Briefly, assays were performed to examine metastatic progression in mice injected with $5\times10^5$ LvM3b cells over-expressing miR-483-5p and miR-551a, with and without CKB over-expression. Liver metastases were monitored by bioluminescent imaging and mice euthanized 35 days after injection. It was found that over-expression of CKB was sufficient to rescue the suppressed liver metastatic phenotypes of cells over-expressing miR-483-5p and miR-551a. Conversely, knockdown of CKB in cells displaying endogenous miR-483-5p or miR-551a inhibition prevented the enhanced metastasis effect seen with miR-483-5p or miR-551a inhibition. To that end, assays were performed to examine liver metastasis in mice injected with $5\times10^5$ SW480 cells whose endogenous miR-483-5p and miR-551a were inhibited by LNA, with and without CKB knockdown. The mice were euthanized after 28 days and liver excised for ex vivo bioluminescence imaging. The results of the above mutational, gain- and loss-of-function experiments, and epistasis analyses reveal CKB to be a direct target of miR-483-5p and miR-551a and to act as a downstream effector of these miRNAs in the regulation of colon cancer metastatic progression. In these assays, P values were found to be less than 0.05 or 0.001 based on one-sided Student's t-tests.

To further confirm the roles of CKB, relative in vivo caspase activities were examined in control SW480 and CKB over-expressing cells in livers of mice. The activities were measured by bioluminescence using a caspase-3 activated DEVD-luciferin and normalized to bioluminescence signal from regular luciferin (n=3). Similar relative in vivo caspase-3 activity were also examined in SW480 cells expressing a control hairpin or hairpin targeting CKB and introduced into the livers of mice through intrasplenic injection. Caspase activities were measured on day 1, day 4 and day 7 after injection. Consistent with the above findings, CKB over-expression significantly reduced, while CKB knockdown significantly enhanced, in vivo caspase-3/7 activity in colon cancer cells during the initial phase of hepatic colonization. In these assays, P values were found to be less than 0.05 or 0.001 based on one-sided Student's t-tests. These findings reveal CKB to be a promoter of colon cancer survival during hepatic metastatic colonization.

EXAMPLE 8

CKB is known to regulate the reservoir of rapidly mobilized high-energy phosphates in tissues such as the brain and kidneys by catalyzing the transfer of a high-energy phosphate group from phosphocreatine to ADP, yielding ATP and creatine. It was hypothesized that CKB generation of ATP from phosphocreatine might provide colon cancer cells with an energetic advantage during hepatic colonization. To determine if ATP, the end-product of CKB catalysis, could rescue metastasis suppression seen upon CKB knockdown, CKB knockdown cells were loaded with ATP prior to injection of cells in experimental metastasis assays. Briefly, liver metastasis was examined in mice injected with $5\times10^5$ LvM3b with or without CKB knockdown and pre-treated with 100 uM ATP or vehicle. Metastatic burden was monitored by bioluminescent imaging and mice euthanized 21 days after injection. It was found that ATP loading of cells was sufficient to significantly enhance the suppressed metastasis phenotype in cells depleted of CKB by more than 10 folds. The rescue by ATP was specific since ATP loading did not enhance the metastatic activity of cells expressing a short-hairpin control.

Similar studies were done to determine whether creatine and phosphocreatine could rescue the phenotype of seen upon CKB knock-down. More specifically, assays were performed to examine liver metastasis in mice injected with $5\times10^5$ LvM3b cells pre-treated with 10 uM creatine, in the background of CKB knockdown. The mice were then euthanized as described above and liver extracted for ex vivo bioluminescent imaging at day 21 after injection. Also, colorectal cancer metastasis was examined in mice injected with $5\times10^5$ LvM3b cells with CKB knockdown and pre-treated with 10 uM creatine-phosphate. Liver metastasis was monitored by bioluminescent imaging and mice were euthanized as described above. It was found that both creatine and creatine-phosphate rescued metastasis suppression.

In order to investigate whether colon cancer metastasis could be inhibited by blocking the transport of creatine into colon cancer cells, the creatine transporter channel SLC6a8 was inhibited in LvM3b cells by expressing short hairpin targeting SLC6a8. Then liver metastasis by LvM3b cells was examined in the same manner described above. It was found that knock-down of the creatine transporter channel SLC6a8 inhibited colon cancer metastasis. These findings reveal that colon cancer cells are dependent on CKB generated ATP for their survival during hepatic colonization.

EXAMPLE 9

In order to determine if this cooperative miRNA regulatory network controlling colon cancer metastatic progression has human pathologic relevance, the expression levels of miR-483-5p and miR-551a were analyzed in a set of 67 primary colon cancers as well as liver metastases obtained from patients at MSKCC. More specifically, miR-483-5p and miR-551a levels in 37 primary tumor samples and 30 liver metastases samples were quantified by quantitative real-time PCR. Consistent with a metastasis-suppressive role for these miRNAs during metastatic progression, miR-483 and miR-551a both displayed significantly reduced expression levels in human liver metastases relative to primary colon cancers (FIG. 1a; p<0.05 for miR-483-5p and p<0.05 for miR-551a; N=67).

CKB expression levels were also examined in the 37 primary tumor samples and 30 liver metastases samples by quantitative real-time PCR. Importantly, CKB expression was found to be significantly elevated in liver metastases relative to primary colon cancers (p<0.05) and its expression was significantly anti-correlated with the miRNAs—consistent with its direct targeting by these miRNAs in human colon cancer (FIG. 1b). These findings are consistent with previous clinical histologic analyses revealing elevated levels of CKB protein in advanced stage cancer.

EXAMPLE 10

In this example, assays were carried out to investigate the therapeutic potential of targeting this miRNA regulatory network. To this end, mice were injected with a high number (500 k) of highly metastatic LvM3a cells and 24 hours later injected mice with a single intra-venous dose of adenoviral-associated virus (AAV) expressing miR-483-5p and miR-551a off a single transcript. It was found that a single therapeutic dose of adeno-associated virus (AAV) delivering both miRNAs dramatically and significantly reduced metastatic colonization by more than 5 fold (FIG. 1c).

Finally, assays were carried out to determine the impact of small-molecule inhibition of CKB and restriction of creatine availability on colon cancer metastasis. Cyclocreatine, which resembles phosphocreatine, is a transition-state analog for creatine kinases. To examine the effect of cyclocreatine, bioluminescent measurements of liver metastasis were carried out in mice injected with $5 \times 10^5$ LvM3b cells and treated with cyclocreatine daily for two weeks. The mice were then euthanized and livers excised for ex vivo imaging at the end of the treatment. It was found that, despite being a poor inhibitor of CKB (5000 uM ki), treatment of mice with cyclocreatine significantly reduced metastatic colonization and proved superior to the current standard-of-care FOLFOX chemotherapy (FIG. 1d).

Similar assays were carried out using a creatine transporter inhibitor beta-guanidinopropionic acid (B-GPA). Bioluminescent measurements were used to examine liver metastasis in mice injected with $5 \times 10^5$ LvM3b cells and treated with B-GPA daily for two weeks. It was found that treatment of mice with this competitive inhibitor of the creatine transporter channel also significantly reduced metastatic colonization (FIG. 1e).

Using a systematic approach, two miRNAs were identified to act as suppressors of liver metastatic colonization by colon cancer cells. It was found find that these miRNAs convergently target CKB—a key gene that endows cells encountering hepatic hypoxia with the ability to generate ATP from phosphocreatine reserves. The successful targeting of this pathway using 4 independent therapeutics that were more effective than the current clinical standard-of-care, and which displayed no apparent toxicity suggest promise for therapeutic targeting of this pathway in human colon cancer. The above-described combined in vivo selection/gene screening approach, which is designated as MUlti-Gene Screening of Human genes through intra-Organ Tandem Selection (MUG-SHOTS) has efficiently identified robust and pathologically validated regulators of liver colonization and metastasis by colon cancer and has the potential to discover coding and non-coding regulators of metastatic colonization of any organ by any cancer type.

EXAMPLE 11

Figure 2:
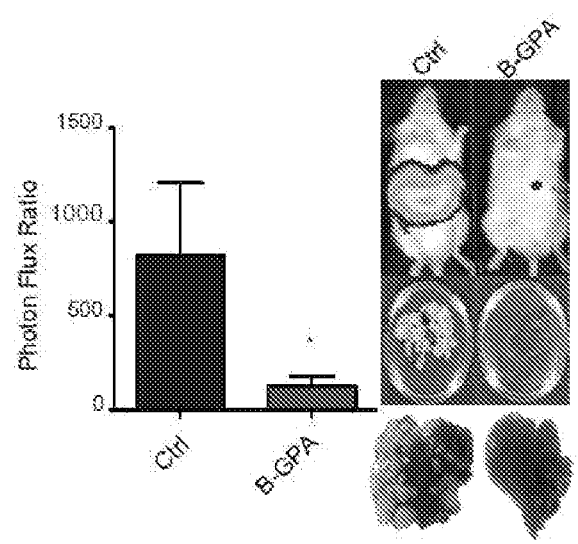
FIG. 2 is a set of s diagram and a photograph showing that B-GPA treatment suppressed colorectal cancer metastasis. Bioluminescent measurements of liver metastasis in mice injected with $5\times10^5$ LvM3b cells and treated with B-GPA daily for three weeks. Mice were euthanized at three weeks and liver extracted for bioluminescent imaging and gross histology. Error bars represent the s.e.m; all P values are based on one-sided Student's t-tests. *P<0.05.

In this example, assays were carried out to confirm the therapeutic potential of targeting the creatine transporter channel SLC6a8 by administering the small molecule B-GPA, which is an inhibitor of SLC6a8. As mentioned above, administration of B-GPA to mice injected with LvM3b colon cancer cells resulted in inhibition of colon cancer metastasis to the liver after two weeks of treatment (FIG. 1e). To confirm this therapeutic effect, mice injected with LvM3b colon cancer cells we treated with either B-GPA or control vehicle (PBS) via intra-peritoneal injection daily for three weeks (FIG. 2). The mice were euthanized at three weeks and liver extracted for bioluminescent imaging and gross histology.

It was found that daily treatment with B-GPA led to a significant reduction in colon cancer metastasis to the liver, as assessed by in vivo bioluminescent imaging of in vivo mice, bioluminescent imaging of extracted liver, and by gross anatomical examination of extracted livers from treated mice (FIG. 2). More specifically, the average photon flux ratios as measure by the bioluminescence imaging for the control group (without treatment of B-GPA) and the treated groups were about 800 and 100, respectively. P values were found to be less than 0.05 based on one-sided Student's t-tests.

EXAMPLE 12

In this example assays were carried out to evaluate the therapeutic benefit of targeting the creatine transporter channel SLC6a8 with shRNA knockdown targeting SLC6a8.

Figure 3:
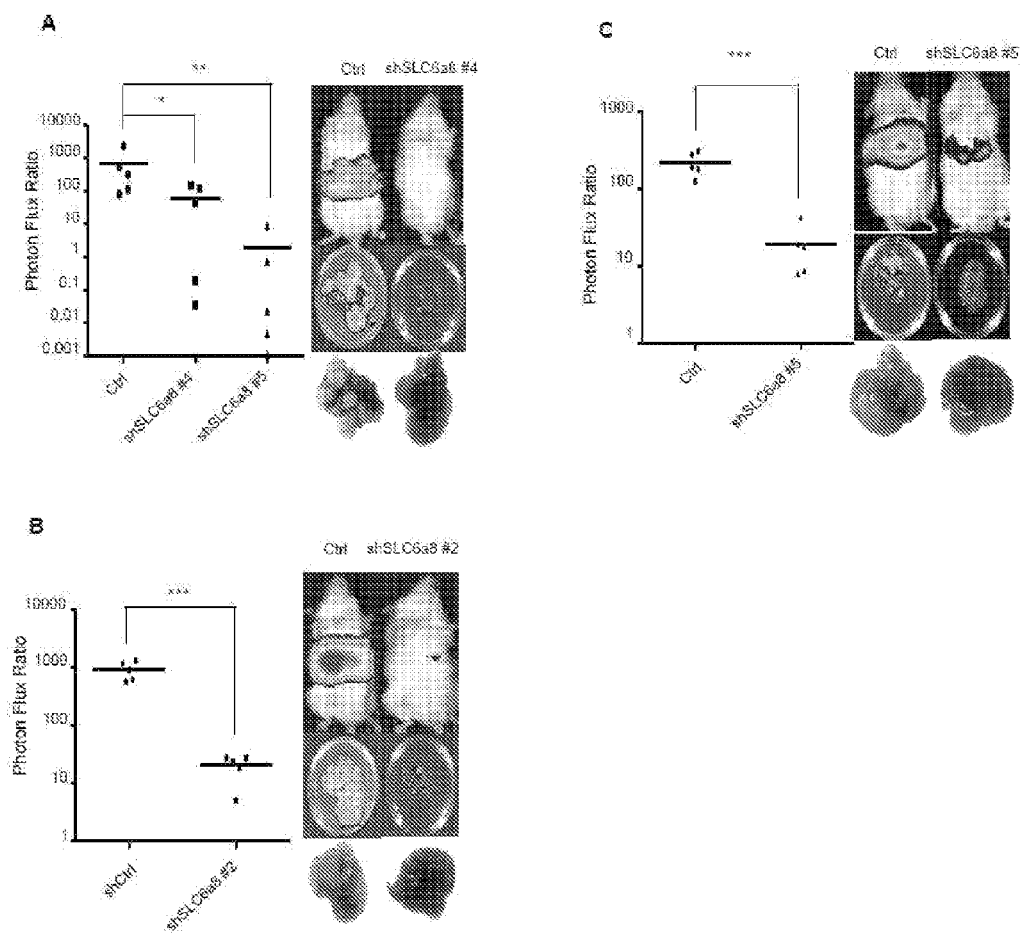
FIGS. 3A-C are a set of diagrams and photographs showing that creatine transporter, SLC6a8 is required for colorectal and pancreatic cancer metastasis. a) Liver metastasis by highly aggressive LvM3b cells expressing short hairpins targeting the creatine transporter channel, SLC6a8. Liver metastasis was monitored by bioluminescent imaging and mice were euthanized three weeks after inoculation of cancer cells. Livers were extracted for gross histology. b) Liver metastasis in mice injected with 5×10[5] SW480 cells transduced with a shRNA targeting SLC6a8. Metastatic progression was monitored by bioluminescent imaging. Mice were euthanized 28 days after injection and livers excised for bioluminescent imaging and gross histology. c) Liver metastasis in mice injected with 5×10[5] PANC1 pancreatic cancer cells transduced with a shRNA targeting SLC6a8. Metastatic progression was monitored by bioluminescent imaging and mice were euthanized as described above. Error bars represent the s.e.m; all P values are based on one-sided Student's t-tests. *P<0.05; P<0.001; *P<0.0001.

Briefly, mice were injected with LvM3b colon cancer cells expressing either of two independent short hairpin RNAs (shSLC6a8 #4 or shSLC6a8 #5) targeting the creatine transporter channel SLC6a8 or with control RNA (empty pLKO vector, ordered from Sigma Aldrich) (FIG. 3a). Again, liver metastasis was monitored by bioluminescent imaging and mice were euthanized three weeks after inoculation of cancer cells. Livers were extracted for gross histology. It was found that knockdown of SLC6a8 with two independent shRNAs resulted in inhibition of colon cancer metastasis (FIG. 3a).

To further confirm the therapeutic benefit of knockdown of SLC6a8, another independent colon cancer cell line (SW480 colon cancer cell line) expressing a short hairpin RNA targeting SLC6a8 (shSLC6a8 #2) was injected into mice (FIG. 3b). It was found that SLC6a8 knockdown significantly inhibited metastasis of SW480 colon cancer cells (FIG. 3b).

Lastly, the therapeutic benefit of targeting SLC6a8 was investigated in pancreatic cancer cells. To accomplish this, PANC1 pancreatic cancer cells expressing either an shRNA targeting SLC6a8 (shSLC6a8 #5) or a control RNA (empty pLKO vector) were injected into mice. Metastatic progression was monitored by bioluminescent imaging and mice were euthanized in the same manner described above. It was found that, at 28 days, there was a significant reduction in pancreatic cancer metastasis in the cells treated with shRNA targeting SLC6a8, revealing that SLC6a8 is a therapeutic target for pancreatic cancer.

EXAMPLE 13

In this example, it was investigated whether expression of the creatine transporter SLC6a8 in human colon cancer tumors correlated with metastatic progression.

Figure 4:
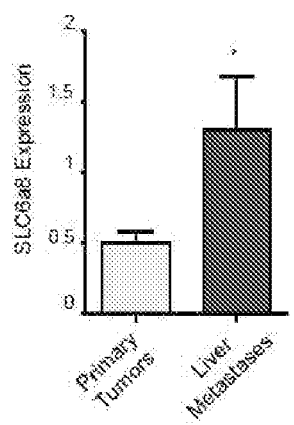
FIG. 4 is diagram showing that SLC6a8 is up-regulated in liver metastases compared to primary tumors. Expression of SLC6a8 in 36 primary tumors and 30 liver metastases were quantified by quantitative real-time PCR. Error bars represent the s.e.m; all P values are based on one-sided Student's t-tests. *P<0.05.
Figure 5:
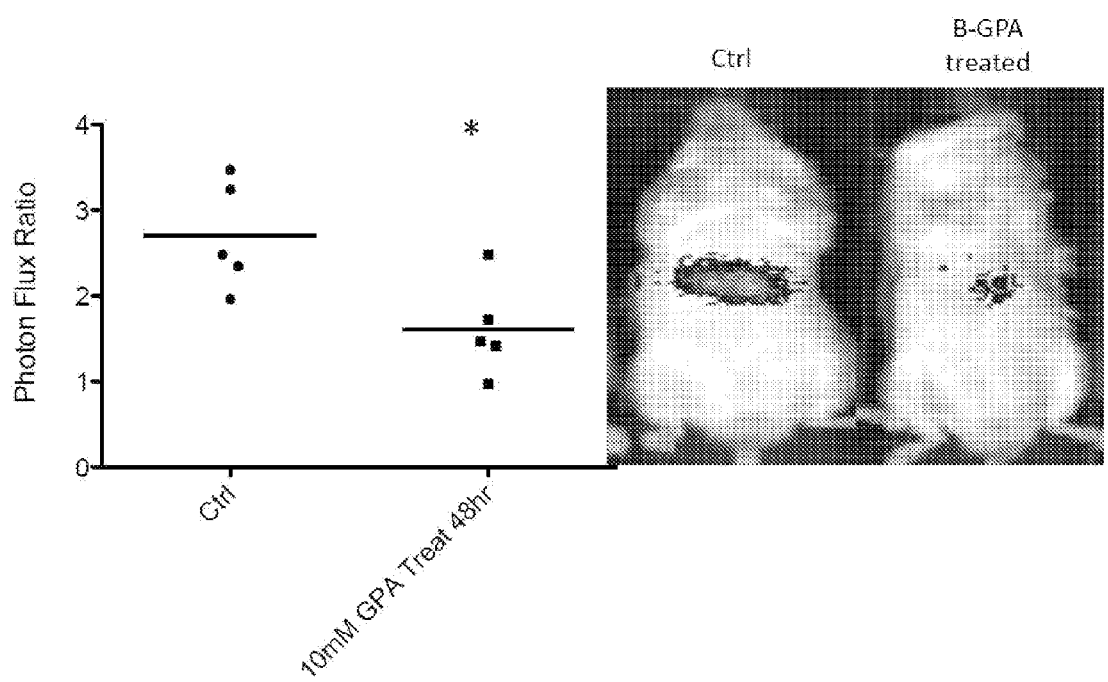
FIG. 5 is a set of a diagram and a photograph showing that B-GPA treatment suppresses survival of disseminated PANC1 pancreatic cancer cells in the liver in vivo. Bioluminescence imaging of immunodeficient mice injected with 5×10[5] PANC1 cells with and without 10 mM B-GPA-pretreatment for 48 hr. Mice were imaged on day 1 after injection and signal was normalized to day zero. P values are based on one-sided Student's t-tests. *P<0.05.

To accomplish this, quantitative real-time PCR was used to quantify the expression of SLC6a8 in 36 primary colon cancer tumors and 30 metastatic colon cancer tumors (FIG. 4). Indeed, expression of SLC6a8 was significantly higher in metastatic tumors (about 1.3) as compared with primary tumors (about 0.5), further confirming the central role of SLC6a8 in metastasis (FIG. 4). P values were found to be less than 0.05 based on one-sided Student's t-tests.

EXAMPLE 14

As mentioned above, it was demonstrated that inhibition of the creatine transporter SLC6a8 with shRNA mediated knock-down resulted in suppression of metastasis of both colon cancer as well as pancreatic cancer. It was also demonstrated that inhibition of SLC6a8 with the small molecule inhibitor B-GPA resulted in therapeutic benefit for colon cancer metastasis in vivo. To evaluate if B-GPA treatment results in therapeutic benefit in pancreatic cancer, the ability of B-GPA treatment to inhibit the survival of human pancreatic cancer cells was assessed in vivo in mice.

Briefly, PANC1 pancreatic cancer cells were incubated for 48 hours with and without the presence of 10 mM of B-GPA, then injected into immunodeficient mice ($5 \times 10^5$ PANC1 cells each mouse; 4 mice each in the treated and untreated cohort). The mice were imaged with bioluminescence imaging on day 1 after injection and signal was normalized to day zero. Therapeutic benefit was observed as early as one day after the injections, with a significant reduction in the tumor burden of pancreatic cancer cells in vivo as assessed by bioluminescence imaging (FIG. 4) demonstrating therapeutic benefit of B-GPA treatment for pancreatic cancer. More specifically, the average photon flux ratios as measure by the bioluminescence imaging for the control group (without treatment of B-GPA) and the treated groups were about 2.7 and 1.6, respectively. P values were found to be less than 0.05 based on one-sided Student's t-tests.

EXAMPLE 15

The above examples demonstrated that B-GPA treatment alone resulted in therapeutic benefit for colon cancer and pancreatic cancer. In this example it was investigated whether B-GPA treatment could enhance the therapeutic activity of the chemotherapy agents 5'-Fluorouracil and Gemcitabine. To accomplish this, cell viability was performed assays to compare the cytotoxic activity of 5'-Fluorouracil or Gemcitabine alone compared with combined therapy with B-GPA.

Figure 6:
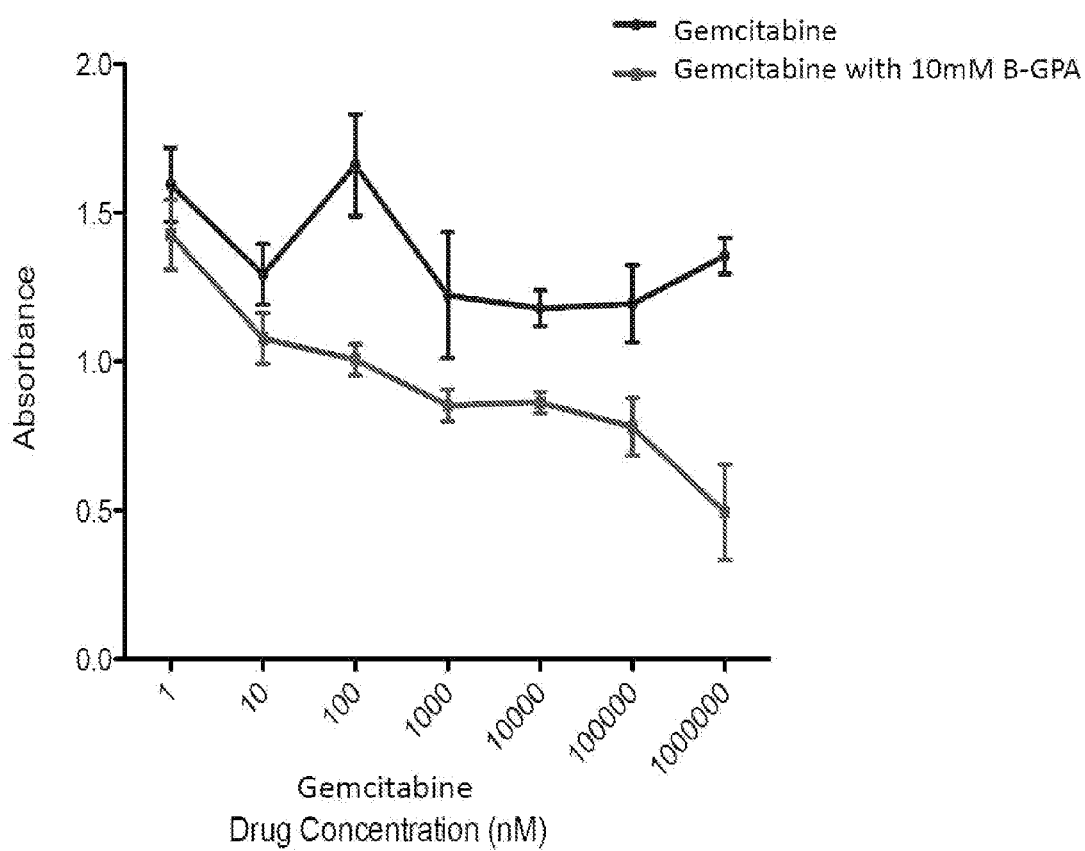
FIG. 6 is a diagram showing that B-GPA enhances the cytotoxicity of Gemcitabine on PANC1 pancreatic cancer cells. Cell viability of PANC1 pancreatic cancer cells after treatment with escalating doses of Gemcitabine alone or escalating doses of Gemcitabine in combination with 10 mM B-GPA. Cell viability was assayed using the WST-1 reagent. Error bars represent standard error of the mean.

Briefly, 10 000 PANC1 cells were seeded in triplicate in 96-well plates and treated with various concentrations of Gemcitabine (1 nm, 10 nm, 100 nm, 1000 nm, 10000 nm, 100000 nm, and 1000000 nm) with or without 10 mM of B-GPA for 48 hours. Cell viability was then assayed using the WST-1 reagent (Roche Applied Science), with absorbance at 440 nm an indicator of the number of viable cells. As shown in FIG. 6, it was found that the addition of a therapeutic concentration of B-GPA enhanced the cytotoxic activity of Gemcitabine on PANC1 pancreatic cancer cells as assessed by a cell viability assay using the WST-1 reagent.

Figure 7:
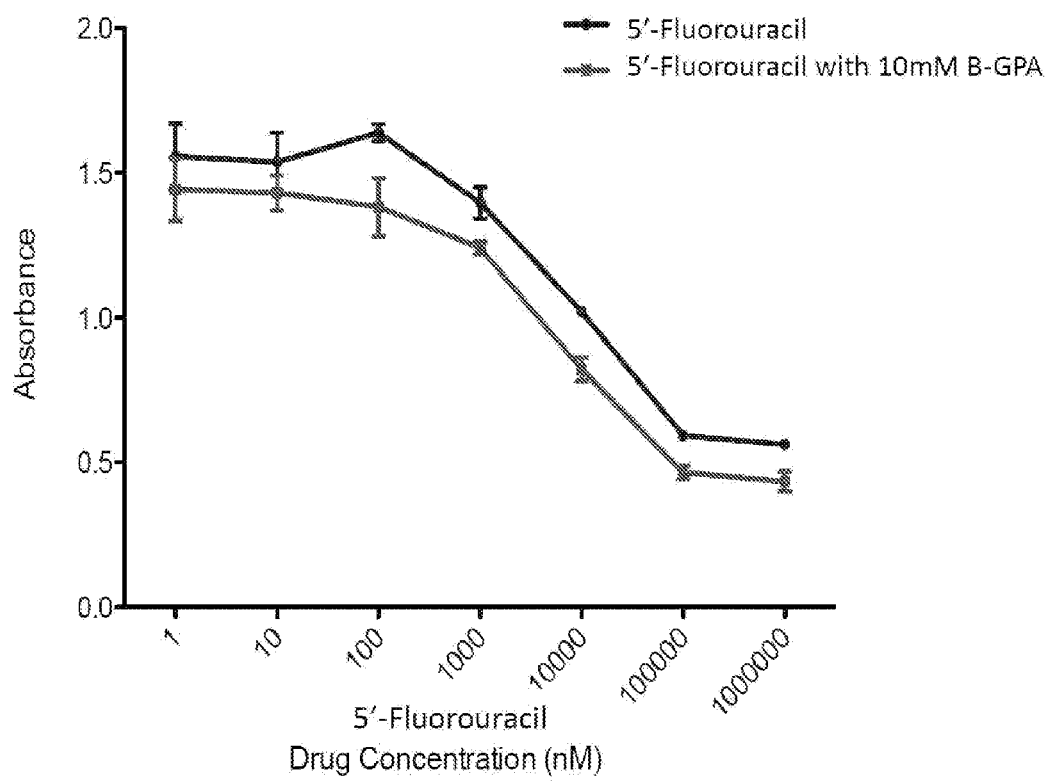
FIG. 7 is a diagram showing that B-GPA enhances the cytotoxicity of 5'-fluorouracil on LS-LvM3b colorectal cancer cells. Cell viability of Ls-LvM3b cells after treatment with escalating doses of 5'-Fluorouracil alone or escalating doses of 5'-Fluorouracil in combination with 10 mM B-GPA. Cell viability was assayed using the WST-1 reagent. Error bars represent standard error of the mean.

Likewise, the addition of a therapeutic concentration of B-GPA enhanced the cytotoxic activity of 5'-Fluorouracil on Ls-LvM3b colon cancer cells. To that end, 10,000 Ls-LvM3b cells were seeded in triplicate in 96-well plates and treated with various concentrations of 5'-Fluorouracil with or without 10 mM of B-GPA for 48 hours. Cell viability was assayed in the same manner described above with absorbance at 440 nm an indicator of the number of viable cells. As shown in FIG. 7, these results demonstrate that B-GPA enhance the therapeutic activity of commonly utilized chemotherapeutic agents for the treatment of colorectal and pancreatic cancer.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated herein in their entireties.

---

What is claimed is:

1. A method for treating a metastatic gastrointestinal cancer in a subject in need thereof, comprising administering to the subject beta-guanidinopropionic acid in an effective amount to suppress metastatic colonization of said gastrointestinal cancer.

2. The method of claim 1, wherein the cancer is even colorectal cancer or pancreatic cancer.

3. The method of claim 1, wherein the cancer is gastric cancer.

4. The method of claim 1, wherein said method comprises the suppression of metastatic colonization of gastrointestinal cancer in the liver in a subject in need thereof.

5. The method of claim 1, further comprising administering to the subject an additional therapeutic agent.

6. The method of claim 5, wherein the additional therapeutic agent is selected from the group consisting of cyclocreatine, a RNAi agent, a nucleic acid, a vector, 5-fluorouracil, Oxaliplatin, Irinotecan, Capecitabine, Gemcitabine, Cetuximab, Taxol, Avastin, folinic acid (leucovorin), Regorafenib, Zaltrap, topoisomerase I inhibitors, NKTR-102, Tivantinib, PX-866, Sorafenib, Linifanib, kinase inhibitors, Telatinib, XL281 (BMS-908662), Robatumumab, and IGF1-R inhibitors.

7. The method of claim 6, wherein the additional therapeutic agent is 5-fluorouracil.

8. The method of claim 6, wherein the additional therapeutic agent is Capecitabine.

9. The method of claim 6, wherein the additional therapeutic agent is Gemcitabine.

10. A method of treating metastatic cancer in a subject in need thereof comprising:
(a) providing a subject identified to have, or to be at risk of having, metastatic cancer on the basis of the expression level of miR-483-5p and/or miR-551a is below a predetermined reference value or the expression level of CKB and/or SLC6a8 is above a predetermined reference value; and
(b) administering to said subject an effective amount of beta-guanidinopropionic acid.

11. The method of claim 10, wherein said cancer is selected from the group consisting of colorectal cancer, pancreatic cancer, gastric cancer, esophageal cancer, liver cancer, breast cancer, prostate cancer, lung cancer, and melanoma.

12. The method of claim 11, wherein said cancer is one of colorectal cancer and gastric cancer.

13. The method of claim 10, further comprising administering to the subject an additional therapeutic agent.

14. The method of claim 13, wherein the additional therapeutic agent is selected from the group consisting of cyclocreatine, a RNAi agent, a nucleic acid, a vector, 5-fluorouracil, Oxaliplatin, Irinotecan, Capecitabine, Gemcitabine, Cetuximab, Taxol, Avastin, folinic acid (leucovorin), Regorafenib, Zaltrap, topoisomerase I inhibitors, NKTR-102, Tivantinib, PX-866, Sorafenib, Linifanib, kinase inhibitors, Telatinib, XL281 (BMS-908662), Robatumumab, and IGF1-R inhibitors.

15. The method of claim 14, wherein the additional therapeutic agent is 5-fluorouracil.

16. The method of claim 14, wherein the additional therapeutic agent is Capecitabine.

17. The method of claim 14, wherein the additional therapeutic agent is Gemcitabine.

18. A method for treating metastatic cancer in a subject in need thereof, comprising contacting creatine transport channel SLC6a8 with beta-guanidinopropionic acid in an amount effective to suppress metastatic colonization of said cancer.

19. The method of claim 18, wherein said method comprises the suppression of metastatic colonization of said cancer in the liver.

20. The method of claim 18, wherein said cancer is selected from the group consisting of colorectal cancer, pancreatic cancer, gastric cancer, esophageal cancer, liver cancer, breast cancer, prostate cancer, lung cancer, and melanoma.

21. The method of claim 20, wherein said cancer is one of colorectal cancer and gastric cancer.

22. The method of claim 18, further comprising administering to the subject an additional therapeutic agent.

23. The method of claim 22, wherein the additional therapeutic agent is selected from the group consisting of cyclocreatine, a RNAi agent, a nucleic acid, a vector, 5-fluorouracil, Oxaliplatin, Irinotecan, Capecitabine, Gemcitabine, Cetuximab, Taxol, Avastin, folinic acid (leucovorin), Regorafenib, Zaltrap, topoisomerase I inhibitors, NKTR-102, Tivantinib, PX-866, Sorafenib, Linifanib, kinase inhibitors, Telatinib, XL281 (BMS-908662), Robatumumab, and IGF1-R inhibitors.

24. The method of claim 23, wherein the additional therapeutic agent is 5-fluorouracil.

25. The method of claim 23, wherein the additional therapeutic agent is Capecitabine.

26. The method of claim 23, wherein the additional therapeutic agent is Gemcitabine.

* * * * *

SEQUENCE LISTING

<160> NUMBER OF SEQ ID NOS: 22

<210> SEQ ID NO 1
<211> LENGTH: 23
<212> TYPE: DNA
<213> ORGANISM: Artificial
<220> FEATURE:
<223> OTHER INFORMATION: Synthetic

<400> SEQUENCE: 1
gaagacggga ggaaagaagg gag                                           23

<210> SEQ ID NO 2
<211> LENGTH: 19
<212> TYPE: DNA
<213> ORGANISM: Artificial
<220> FEATURE:
<223> OTHER INFORMATION: Synthetic

<400> SEQUENCE: 2
gacccactct tggtttcca                                                19

<210> SEQ ID NO 3

```
<211> LENGTH: 76
<212> TYPE: DNA
<213> ORGANISM: Artificial
<220> FEATURE:
<223> OTHER INFORMATION: Synthetic

<400> SEQUENCE: 3
gagggggaag acggaggaa agaagggagt ggttccatca cgcctcctca ctcctctcct      60
cccgtcttct cctctc                                                    76

<210> SEQ ID NO 4
<211> LENGTH: 96
<212> TYPE: DNA
<213> ORGANISM: Artificial
<220> FEATURE:
<223> OTHER INFORMATION: Synthetic

<400> SEQUENCE: 4
ggggactgcc gggtgaccct ggaaatccag agtgggtggg gccagtctga ccgtttctag    60
gcgacccact cttggtttcc agggttgccc tggaaa                              96

<210> SEQ ID NO 5
<211> LENGTH: 559
<212> TYPE: DNA
<213> ORGANISM: Artificial
<220> FEATURE:
<223> OTHER INFORMATION: Synthetic miR-483-5p

<400> SEQUENCE: 5
cctgccccat tgggggtag gaagtggcac tgcagggcct ggtgccagcc agtccttgcc      60
cagggagaag cttccctgca ccaggctttc ctgagaggag gggagggcca agcccccact   120
tgggggaccc ccgtgatggg gctcctgctc cctcctccgg ctgatggcac ctgcccttg    180 gcaccccaag gtggagcccc cagcgacctt cccctttccag ctgagcattg ctgtggggga  240
gagggggaag acgggaggaa agaagggagt ggttccatca cgcctcctca ctcctctcct   300
cccgtcttct cctctcctgc ccttgtctcc ctgtctcagc agctccaggg gtggtgtggg   360
cccctccagc ctcctaggtg gtgccaggcc agagtccaag ctcagggaca gcagtccctc   420 ctgtggggggc ccctgaactg ggctcacatc ccacacattt tccaaaccac tcccattgtg  480
agcctttggt cctggtggtg tccctctggt tgtgggacca agagcttgtg cccattttc    540 atctgaggaa ggaggcagc                                                559

<210> SEQ ID NO 6
<211> LENGTH: 490
<212> TYPE: DNA
<213> ORGANISM: Artificial
<220> FEATURE:
<223> OTHER INFORMATION: Synthetic miR-551a

<400> SEQUENCE: 6
ggagaacctt cagcttcatg tgacccagag actcctgtat gcctggctct ggagtacag     60 aagggcctag agctgacccc tgccctccga agccctggg gcactagatg gatgtgtgcc   120
agagggtagt agaggcctgg gggtagagcc cagcaccccc ttcgcgtaga gacctggggg   180
accagccagc ccagcaaccc cctcgcggcc gacgcctgag gctgttcctg gctgctccgg  240
tggctgccag aggggactgc cgggtgaccc tggaaatcca gagtgggtgg ggccagtctg   300
accgtttcta ggcgacccac tcttggtttc cagggttgcc ctggaaacca cagatgggga   360
ggggttgatg gcacccagcc tcccccaagc ctggaaggg acccggatc cccagagcct    420
```

```
ttccctgcct atggagcgtt tctcttggag aacagggggg cctctcagcc cctcaatgca    480
agttgctgag                                                           490
```

<210> SEQ ID NO 7
<211> LENGTH: 19
<212> TYPE: RNA
<213> ORGANISM: Artificial
<220> FEATURE:
<223> OTHER INFORMATION: Synthetic

<400> SEQUENCE: 7

```
gacccacucu ugguuucca                                                  19
```

<210> SEQ ID NO 8
<211> LENGTH: 96
<212> TYPE: RNA
<213> ORGANISM: Artificial
<220> FEATURE:
<223> OTHER INFORMATION: Synthetic

<400> SEQUENCE: 8

```
ggggacugcc gggugacccu ggaaauccag aguggguggg ccagucuga ccguuucuag     60 gcgacccacu cuugguuucc agggttugccc uggaaa                              96
```

<210> SEQ ID NO 9
<211> LENGTH: 23
<212> TYPE: RNA
<213> ORGANISM: Artificial
<220> FEATURE:
<223> OTHER INFORMATION: Synthetic

<400> SEQUENCE: 9

```
gaagacggga ggaaagaagg gag                                             23
```

<210> SEQ ID NO 10
<211> LENGTH: 23
<212> TYPE: RNA
<213> ORGANISM: Artificial
<220> FEATURE:
<223> OTHER INFORMATION: Synthetic

<400> SEQUENCE: 10

```
gaagacggga ggaaagaagg gag                                             23
```

<210> SEQ ID NO 11
<211> LENGTH: 57
<212> TYPE: DNA
<213> ORGANISM: Artificial
<220> FEATURE:
<223> OTHER INFORMATION: Synthetic

<400> SEQUENCE: 11

```
ccggcccaga ttgaaactct cttcactcga gtgaagagag tttcaatctg ggttttt       57
```

<210> SEQ ID NO 12
<211> LENGTH: 59
<212> TYPE: DNA
<213> ORGANISM: Artificial
<220> FEATURE:
<223> OTHER INFORMATION: Synthetic

<400> SEQUENCE: 12

```
ccggccgcgg tatctggcac aatgactcga gtcattgtgc cagataccgc ggttttttg     59
```

<210> SEQ ID NO 13
<211> LENGTH: 58
<212> TYPE: DNA
<213> ORGANISM: Artificial
<220> FEATURE:
<223> OTHER INFORMATION: Synthetic

<400> SEQUENCE: 13
ccggcttatt ccctacgtcc tgatcctcga ggatcaggac gtagggaata agtttttg    58

<210> SEQ ID NO 14
<211> LENGTH: 58
<212> TYPE: DNA
<213> ORGANISM: Artificial
<220> FEATURE:
<223> OTHER INFORMATION: Synthetic

<400> SEQUENCE: 14
ccggattacc tggtcaagtc ctttactcga gtaaaggact tgaccaggta attttttg    58

<210> SEQ ID NO 15
<211> LENGTH: 57
<212> TYPE: RNA
<213> ORGANISM: Artificial
<220> FEATURE:
<223> OTHER INFORMATION: Synthetic

<400> SEQUENCE: 15
ccggcccaga uugaaacucu cuucacucga gugaagagag uuucaaucug gguuuuu     57

<210> SEQ ID NO 16
<211> LENGTH: 59
<212> TYPE: RNA
<213> ORGANISM: Artificial
<220> FEATURE:
<223> OTHER INFORMATION: Synthetic

<400> SEQUENCE: 16
ccggccgcgg uaucuggcac aaugacucga gucaugugc cagauaccgc gguuuuug     59

<210> SEQ ID NO 17
<211> LENGTH: 58
<212> TYPE: RNA
<213> ORGANISM: Artificial
<220> FEATURE:
<223> OTHER INFORMATION: Synthetic

<400> SEQUENCE: 17
ccggcuuauu cccuacgucc ugauccucga ggaucaggac guagggaaua aguuuug     58

<210> SEQ ID NO 18
<211> LENGTH: 58
<212> TYPE: RNA
<213> ORGANISM: Artificial
<220> FEATURE:
<223> OTHER INFORMATION: Synthetic

<400> SEQUENCE: 18
ccggauuacc uggucaaguc cuuuacucga guaaaggacu ugaccaggua auuuuuug    58

<210> SEQ ID NO 19
<211> LENGTH: 58
<212> TYPE: DNA
<213> ORGANISM: Artificial
<220> FEATURE:
<223> OTHER INFORMATION: Synthetic

```
<400> SEQUENCE: 19
ccgggctggt ctacaacaac acctactcga gtaggtgttg ttgtagacca gcttttg          58

<210> SEQ ID NO 20
<211> LENGTH: 58
<212> TYPE: RNA
<213> ORGANISM: Artificial
<220> FEATURE:
<223> OTHER INFORMATION: Synthetic

<400> SEQUENCE: 20
ccgggcuggu cuacaacaac accuacucga guagguguug uuguagacca gcuuuuug         58

<210> SEQ ID NO 21
<211> LENGTH: 22
<212> TYPE: DNA
<213> ORGANISM: Artificial
<220> FEATURE:
<223> OTHER INFORMATION: Synthetic forward primer

<400> SEQUENCE: 21
ggcagctaca accgcttcaa ca                                                22

<210> SEQ ID NO 22
<211> LENGTH: 22
<212> TYPE: DNA
<213> ORGANISM: Artificial
<220> FEATURE:
<223> OTHER INFORMATION: Synthetic reverse primer

<400> SEQUENCE: 22
caggatggag aagaccacga ag                                                22
```